US008601878B2

(12) United States Patent
Cotrell et al.

(10) Patent No.: US 8,601,878 B2
(45) Date of Patent: Dec. 10, 2013

(54) BASE EXCITATION TESTING SYSTEM USING SPRING ELEMENTS TO PIVOTALLY MOUNT WIND TURBINE BLADES

(75) Inventors: Jason Cotrell, Golden, CO (US); Scott Hughes, Golden, CO (US); Sandy Butterfield, Golden, CO (US); Scott Lambert, Boulder, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 461 days.

(21) Appl. No.: 12/990,069

(22) PCT Filed: May 1, 2009

(86) PCT No.: PCT/US2009/042537
§ 371 (c)(1),
(2), (4) Date: Oct. 28, 2010

(87) PCT Pub. No.: WO2009/135136
PCT Pub. Date: Nov. 5, 2009

(65) Prior Publication Data
US 2011/0041617 A1    Feb. 24, 2011

Related U.S. Application Data

(63) Continuation-in-part of application No. PCT/US2008/086662, filed on Dec. 12, 2008.

(60) Provisional application No. 61/049,903, filed on May 2, 2008.

(51) Int. Cl.
| | |
|---|---|
| *G01M 7/06* | (2006.01) |
| *F03D 11/00* | (2006.01) |
| *F03D 11/04* | (2006.01) |
| *G01M 13/00* | (2006.01) |
| *G01N 3/32* | (2006.01) |
| *G01M 7/02* | (2006.01) |
| *G01N 3/02* | (2006.01) |

(52) U.S. Cl.
CPC ......... *F03D 11/0091* (2013.01); *F03D 11/045* (2013.01); *F05B 2250/42* (2013.01); *F05B 2260/83* (2013.01); *G01M 7/027* (2013.01); *G01M 7/06* (2013.01); *G01N 3/02* (2013.01); *G01N 3/32* (2013.01); *G01N 2203/0035* (2013.01); *G01N 2203/0073* (2013.01)
USPC .............. 73/663; 73/118.01; 73/577; 73/794; 73/806; 73/856; 73/865.9

(58) Field of Classification Search
CPC ..... F03D 11/00; F03D 11/0091; F03D 11/04; F03D 11/045; F05B 2250/42; F05B 2260/83; G01M 7/025; G01M 7/027; G01M 7/06; G01M 13/00; G01M 99/00; G01N 3/02; G01N 3/32; G01N 2033/083; G01N 2203/0035; G01N 2203/0073; Y02E 10/72; Y02E 10/722
USPC ............ 73/116.03–116.04, 118.01, 577–579, 73/584, 593, 649, 660, 663, 794, 806, 808, 73/856, 865.3, 865.9, 866.4; 290/44, 55; 415/4.1–4.2, 118
See application file for complete search history.

(56) References Cited

U.S. PATENT DOCUMENTS

| | | | | |
|---|---|---|---|---|
| 2,127,950 | A * | 8/1938 | Bennett | 73/474 |
| 3,100,989 | A * | 8/1963 | Jones | 73/862.381 |
| 4,389,891 | A | 6/1983 | Fournier | |
| 5,974,882 | A | 11/1999 | Heath | |
| 6,094,989 | A | 8/2000 | Twerdochlib | |
| 6,394,745 | B1 | 5/2002 | Quraeshi | |
| 7,362,004 | B2 | 4/2008 | Becker | |
| 7,946,802 | B1 | 5/2011 | Iskrenovic | |
| 8,092,182 | B2 | 1/2012 | Radisek | |
| 8,096,773 | B2 | 1/2012 | Chang | |
| 8,100,651 | B2 | 1/2012 | Tsou | |
| 8,393,216 | B2 * | 3/2013 | Guy | 73/577 |
| 2006/0037402 | A1 | 2/2006 | Musial et al. | |
| 2007/0272018 | A1 | 11/2007 | Shadman et al. | |
| 2010/0263448 | A1 * | 10/2010 | Hughes et al. | 73/577 |
| 2010/0275695 | A1 * | 11/2010 | Cotrell et al. | 73/663 |
| 2011/0179884 | A1 * | 7/2011 | Guy | F05B 2260/83 |
| 2011/0292372 | A1 * | 12/2011 | Criado Abad et al. | F05B 2260/83 |
| 2012/0020798 | A1 * | 1/2012 | Barnsley | F05B 2260/83 |
| 2012/0314201 | A1 * | 12/2012 | Riezu Corpas et al. | 356/32 |

| | | | | |
|---|---|---|---|---|
| 2013/0061683 A1* | 3/2013 | Baker et al. | | 73/856 X |
| 2013/0071244 A1* | 3/2013 | Mertens et al. | | 290/55 X |
| 2013/0213136 A1* | 8/2013 | Guy | | 73/577 |

FOREIGN PATENT DOCUMENTS

| | | | | |
|---|---|---|---|---|
| JP | 04164231 | | 6/1992 | |
| SU | 779846 B | * | 11/1980 | ............ G01M 17/00 |
| WO | 2004005879 A1 | | 1/2004 | |

OTHER PUBLICATIONS

International Search Report dated Aug. 14, 2009, for Intl Application No. PCT/US08/86662.

Written Opinion dated Aug. 14, 2009, for Intl Application No. PCT/US08/86662.

International Search Report/Written Opinion dated Dec. 4, 2009, for Intl Application No. PCT/US09/42537.

White, "New Method for Dual-Axis Fatigue Testing of Large Wind Turbine Blades Using Resonance Excitation and Spectral Loading", NREL Technical Report, Apr. 2004, (NREL/TP 500-35268), pp. 1-185.

Veers, "A General Method for Fatigue Analysis of Vertical Axis Wind Turbine Blades", SAND82-2543, Sandia National Laboratories, Oct. 1983, pp. 3-8 + 6 more pages.

Rumsey et al., "Structural Health Monitoring of Wind Turbine Blades", Sandia National Laboratories, 2008, accessed at www. http://windpower.sandia.gov/other/SPIE-2008-6933-14.pdf on Jul. 9, 2013, pp. 1-15.

International Preliminary Report on Patentability for International (PCT) Application No. PCT/US09/42537, issued Nov. 2, 2010, pp. 1-5.

International Preliminary Report on Patentability for International (PCT) Application No. PCT/US08/86662, issued Jun. 15, 2010, pp. 1-5.

* cited by examiner

*Primary Examiner* — Thomas P Noland

(74) *Attorney, Agent, or Firm* — W. LaNelle Owens; Paul J. White; John C. Stolpa

(57) ABSTRACT

A system (1100) for fatigue testing wind turbine blades (1102) through forced or resonant excitation of the base (1104) of a blade (1102). The system (1100) includes a test stand (1112) and a restoring spring assembly (1120) mounted on the test stand (1112). The restoring spring assembly (1120) includes a primary spring element (1124) that extends outward from the test stand (1112) to a blade mounting plate (1130) configured to receive a base (1104) of blade (1102). During fatigue testing, a supported base (1104) of a blade (1102) may be pivotally mounted to the test stand (1112) via the restoring spring assembly (1120). The system (1100) may include an excitation input assembly (1140) that is interconnected with the blade mounting plate (1130) to selectively apply flapwise, edgewise, and/or pitch excitation forces. The restoring spring assembly (1120) may include at least one tuning spring member (1127) positioned adjacent to the primary spring element (1124) used to tune the spring constant or stiffness of the primary spring element (1124) in one of the excitation directions.

20 Claims, 14 Drawing Sheets

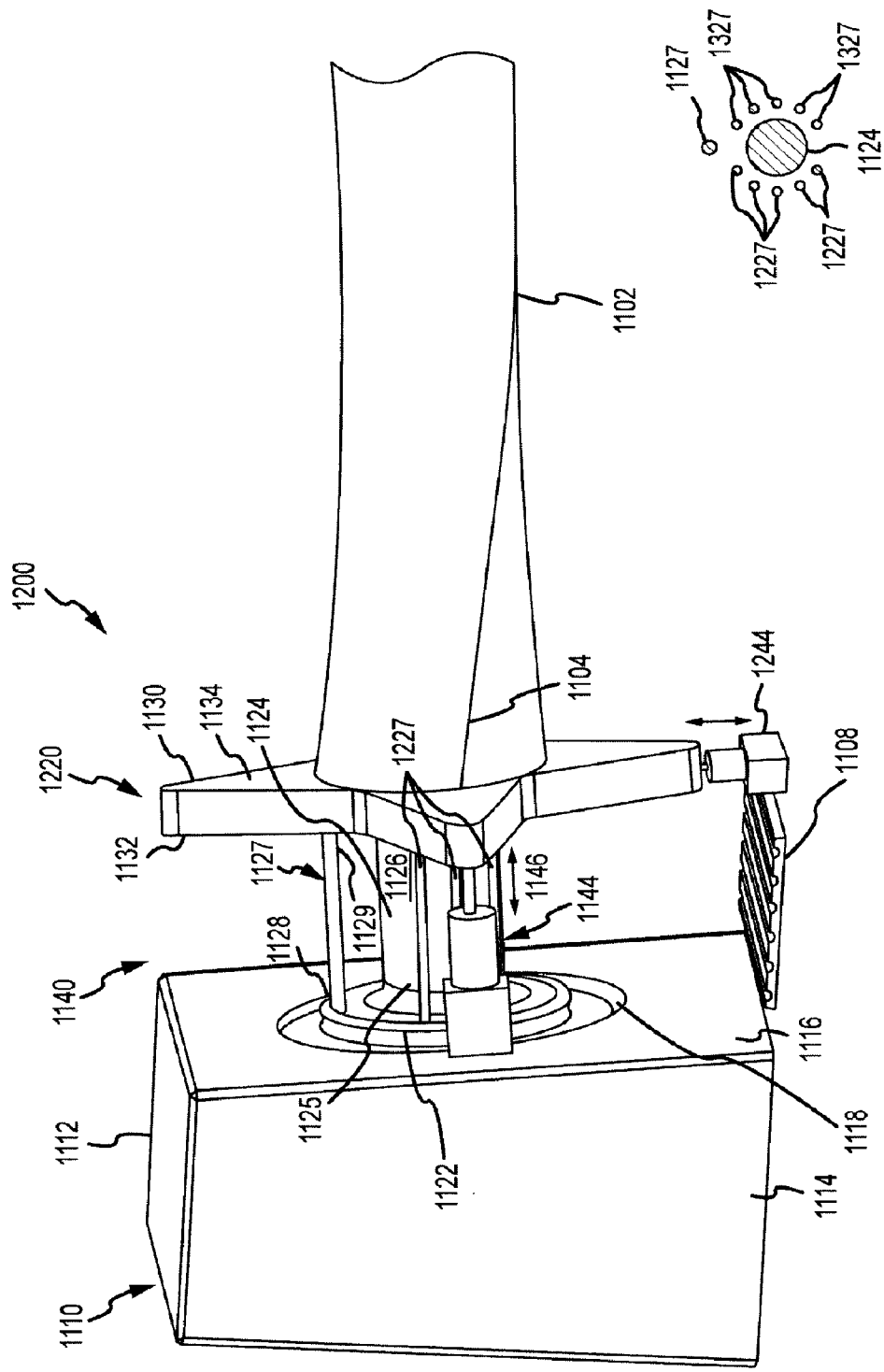

BASE EXCITATION TESTING SYSTEM USING SPRING ELEMENTS TO PIVOTALLY MOUNT WIND TURBINE BLADES

CROSS-REFERENCE TO RELATED APPLICATIONS

This application is a continuation-in-part of PCT Appl. No. PCT/US08/86662 filed Dec. 12, 2008, and this application also claims the benefit of U.S. Provisional Application No. 61/049,903, filed on May 2, 2008. Both of these applications are incorporated herein by reference in their entireties.

CONTRACTUAL ORIGIN

The United States Government has rights in this invention under Contract No. DE-AC36-08GO28308 between the United States Department of Energy and the Alliance for Sustainable Energy, LLC, the manager and operator of the National Renewable Energy Laboratory.

BACKGROUND

Recently, there has been a rapidly growing demand for renewable energy including wind energy. To meet this demand, wind turbine designers are working to provide blade designs that allow a turbine connected to the wind turbine blades or to the rotor to effectively convert wind into electricity. The blades must also be designed properly to withstand inertial forces, aerodynamic forces, and structural forces so as to provide a relatively long service life and safe operation. Like all rotating machines, wind turbines are generators of fatigue, and every revolution of its components including the turbine blades produces a load or fatigue cycle, with each of these cycles causing a small, finite amount of damage that eventually may lead to fatigue cracks or other failures.

Modeling may be used in some cases to determine service life of a turbine blade during normal operations. However, modeling has its limitations including variations in the as-built/manufactured blade and a design and the difficulty in accurately modeling operational conditions with varying and sometimes random loading. As a result, wind turbine blades are typically laboratory tested to determine that their fatigue strength and characteristics are adequate for a desired service life. Wind turbine or rotor blade testing is used to verify that laminations in the blade are safe (e.g., the layers used to fabricate a blade do not separate (i.e., delamination)) and to verify that the blade will not break under repeated stress.

Presently, wind turbine blades are fatigue tested in the flapwise direction (i.e., out of the rotor plane or in a direction transverse to a plane extending through the blade) and in the edgewise direction (i.e., in the plane of rotation or in a direction parallel to a plane extending through the blade). For large blades (e.g., greater than 40-meter blade lengths), these two fatigue tests (e.g., two single axis tests) are typically run sequentially, and, to simulate a typical service life of a blade, each test may involve placing a blade through 1 million to 10 million or more load or fatigue cycles, which may take 3 to 12 months or more to complete for each tested direction. There is a trend for wind generator systems to become increasingly larger. Unfortunately, however, the larger blades associated with larger wind generator systems are subjected to greater static and dynamic loads and the facilities required to test these larger blades are also very large as newer generation turbine generators being designed with blades 40 meters or more in length. It is very desirable, and often necessary, to advance test a proposed blade design to ensure that it will be capable of withstanding the expected loads without structural failure and to evaluate the fatigue resistance of the blade design, and these advanced tests may significantly delay implementation of a new blade design. The test equipment can also be relatively expensive to purchase and operate, which can drive up the costs of blades and wind energy. Hence, there is a need for blade testing techniques that are less expensive to use and require less time to complete while still providing accurate fatigue testing results.

As further background on laboratory testing, wind turbine blades are tested by applying loads to the blade in various directions. For example, one type of load is applied in a direction perpendicular to the longitudinal or long axis of the blade and is often referred to as a bending load or as a flap load in the wind turbine field. Another type of load is also applied in a direction perpendicular to the longitudinal axis but also perpendicular to the direction of the applied bending or flap load in order to assess the structural properties of the blade in the transverse or rotational direction. Such loads are often referred to as transverse or lead-lag loads. The load applied to the blade in a given direction may be time-invariant or "static." Alternatively, the load may be made to vary with time in which case the load is often referred to as "cyclic." Static loads are generally useful in evaluating the stiffness and ultimate strength of the blade whereas cyclic loads are generally useful in evaluating the fatigue resistance of the blade.

Several different types of test systems have been developed and are being used to apply loads to wind turbine blades. One type of test system uses a linear hydraulic actuator to apply the desired loads to the blade. The base or root of the blade is mounted to a rigid and very large test stand and the linear hydraulic actuator is mounted to the blade some distance from the root or base and from the test stand. This type of apparatus is advantageous in that it can be used to apply loads in any desired direction by simply mounting the hydraulic actuators at the desired positions on the blade and by orienting the actuators in the appropriate directions, e.g., for sequential flapwise and edgewise testing. However, these systems require a large actuator, and a relatively complex hydraulic system with pumps and hoses to operate the actuator to oscillate the blade or test article. The size of the test stand with its large concrete blocks and the complexity and size of the hydraulic actuator make these testing systems difficult to move and time consuming and expensive to build and set up, which limits the number of such test systems and forces blade manufacturers to ship blades to the testing facilities for fatigue testing.

More recently, a resonance test system has been designed and used that provides an actuator for applying loads in the flapwise direction at or near the resonant or natural frequency of the test system in the flapwise direction. The loading apparatus is attached directly or through compliant linkages to the blade (e.g., at a location some distance from the blade base or root such as one third or more along the length of the blade). A transverse load, in some cases, is applied (e.g., a load in the edgewise direction) to the edge of the blade to load the blade in the edgewise direction at the same time as it is loaded in the flapwise direction to better simulate actual operating loads and hasten testing. For example, the transverse load has typically been applied with a forced displacement device with a bell crank or similar device that is attached to the ground plane to provide oscillation in the edgewise or transverse direction. The oscillation in the transverse direction is typically provided at the same frequency used for the actuator applying a flapwise load (e.g., both loads are input at or near the resonant frequency of the test system in the flapwise direction), and the design of the forced displacement device has limited capability due to the large oil flow, if utilizing hydraulic systems, and displacement requirements. As a result, such fatigue testing systems are possible but may be limited by practical constraints for larger blades (e.g., blades over 40 meters) in which flapwise displacement may be quite large such as up to 6 meters or more. Again, blade excitation is imparted at locations spaced apart from the blade base or root.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other improvements.

Briefly, multi-axis degree of freedom blade testing systems are described that effectively utilize base excitation (e.g., shaking or oscillating a base or root) to provide more efficient fatigue testing of wind turbine blades. During operation, the system provides a testing method that provides simultaneous displacements of a test article such as a blade in multiple degrees-of-freedom (e.g., translations and/or rotations) by concurrently moving or shaking a blade support structure in two or more directions. To allow smaller actuators to be used and to reduce the use of large bearing mechanisms, the testing systems may include restoring spring assemblies that are used to pivotally mount a base of a blade or test article to a rigid test stand. The restoring spring assemblies, for example, may include a relatively large primary spring element to support a blade base and also function to provide forces that return the blade base to an original or at rest position upon removal of excitation forces. The restoring spring assemblies may also be tunable as one or more tuning springs may be included to adjust stiffness or tune a restoring spring assembly spring constant to provide higher quality fatigue testing, e.g., testing in which the testing system natural frequency is more closely matched to a resonant frequency of a tested turbine blade.

More particularly, an apparatus or system is provided for fatigue testing elongate test articles including wind turbine blades through forced or resonant excitation of the base of the test articles. The apparatus includes a test stand, which may be positioned and/or supported on a testing platform. The apparatus also includes a restoring spring assembly that is mounted on the test stand such as with a base affixed to a vertical side or face of the test stand. The restoring spring assembly includes a primary spring element that extends outward from the test stand to a blade mounting plate, with some embodiments having the primary spring element coupled at a first end to the test stand and coupled at a second end to the blade mounting plate. During use of the apparatus for fatigue testing, a supported base of a blade or other test article may be pivotally mounted to the test stand via the restoring spring assembly. The apparatus may also include an excitation input assembly that is interconnected with the blade mounting plate to selectively apply excitation forces in at least first and second directions (with the second direction typically differing from the first such as when the first direction provides horizontal or edgewise excitation of a blade while the second direction provides vertical or flapwise excitation of a blade).

In some embodiments, the restoring spring assembly may include at least one tuning spring member positioned adjacent to the primary spring element and extending between the test stand and the blade mounting plate. The test article may be a wind turbine blade and the first and second directions may correspond to flapwise and edgewise directions of the wind turbine blade. In this case, a tuning spring member(s) may be provided to increase stiffness of the restoring spring assembly in the flapwise direction and/or in the edgewise direction. The tuning spring members may take a variety of forms, with one example being a solid metal or other material rod typically with an outer diameter significantly less than the primary spring element (e.g., an OD of up to several inches while the primary spring element may be a solid metallic shaft with an OD of 8 to 10 inches or more and a length of at least about 18 inches). The blade mounting plate may include an inner side proximate to or facing the test stand (e.g., extending transverse to a longitudinal axis of the primary spring element), and the excitation input assembly may include one or more actuators mounted to the test stand and coupled to the inner side of the blade mounting plate, whereby the actuator(s) provide all or a portion of the excitation forces for the blade base. In other cases, the excitation input assembly may include one or more actuators attached to the ground, a testing platform, or other support and applying all or portions of the excitation forces to the blade mounting plate (such as in a substantially vertical direction to an edge of the plate or the like).

In addition to the exemplary aspects and embodiments described above, further aspects and embodiments will become apparent by reference to the drawings and by study of the following descriptions.

BRIEF DESCRIPTION OF THE DETAILED DRAWINGS

Exemplary embodiments are illustrated in referenced figures of the drawings. It is intended that the embodiments and figures disclosed herein are to be considered illustrative rather than limiting.

FIG. 1 illustrates in schematic and/or functional block form a base excitation test system for use in load and/or fatigue testing a test article or specimen such as a blade for a wind turbine, with the test system being adapted to act on the base or root of the blade to impart oscillating or excitation forcing loads or functions in one, two, three, and/or more directions or degrees of freedom separately or concurrently (e.g., actuation in the flap direction, actuation in the edge direct, pitch actuation, and so on) on the test article or blade;

FIG. 12 illustrates a BETS similar to that shown in FIG. 11 with a differing excitation input assembly and a differing arrangement of additional or tuning spring members positioned about a primary spring element;

FIG. 13 illustrates a sectional view of the restoring spring assembly of FIG. 12 showing use of a multiple tuning springs or spring members to achieve a desired system resonance or natural frequency to suit a particular blade or test;

DESCRIPTION

Figure 1:
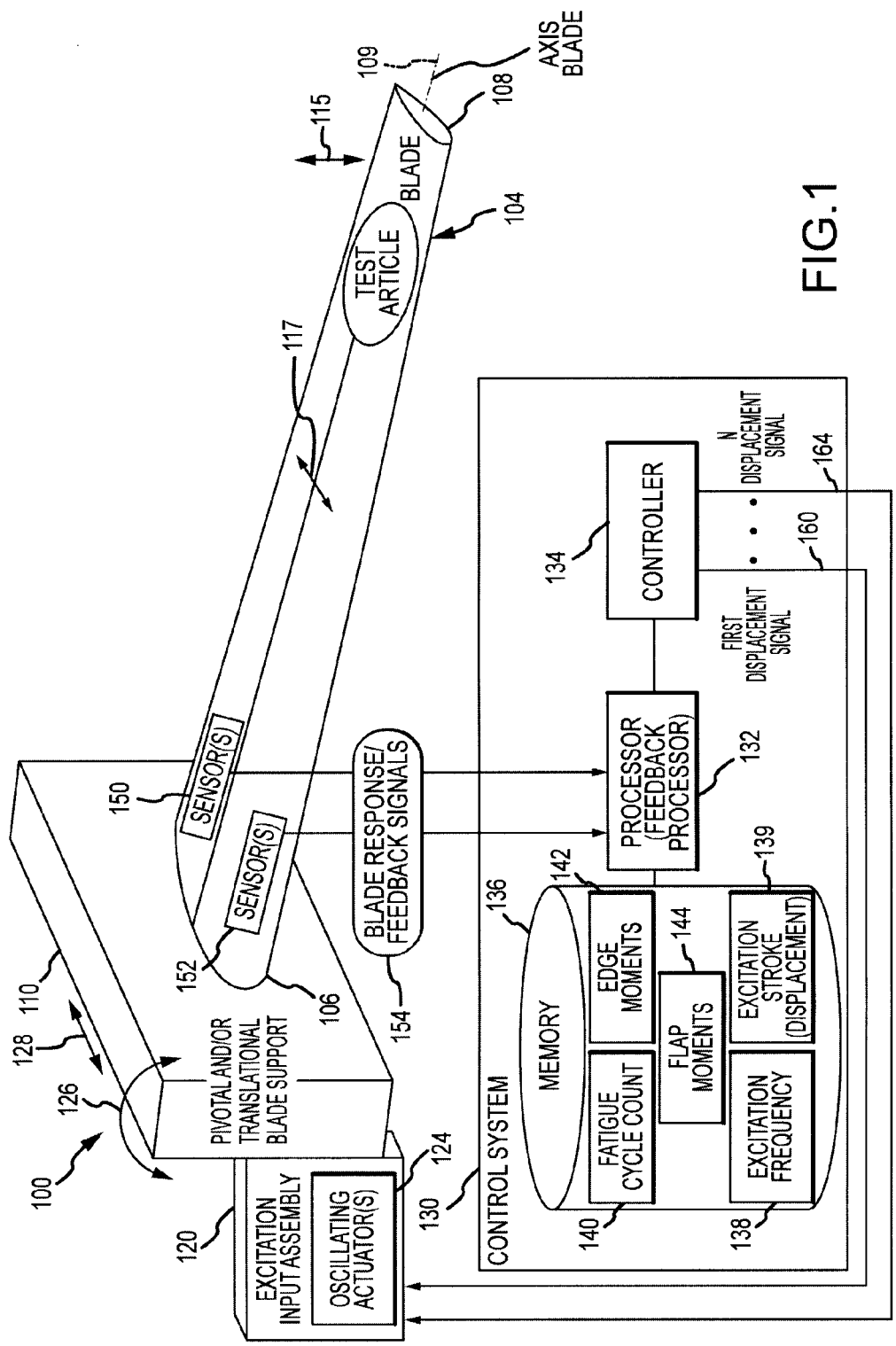

The following provides a description of exemplary methods and systems for fatigue testing wind turbine blades through use of base or root excitation. Generally, embodiments described herein use a variety of techniques to shake or excite a blade support (e.g., a test stand) so as to cause a test article such as wind turbine blade to oscillate in one or more directions or in one or more degrees of freedom. For example, a blade may be mounted to a blade support, and the blade support may be oscillated in a first direction (e.g., in the flapwise (or out of the rotor plane) direction) and concurrently oscillated in a second direction (e.g., in the edgewise (or in the rotor plane) direction). In prior blade testing, fatigue in these two directions or axes of the blade were typically performed independently by applying loads and/or forcing functions to the blade at a location spaced apart from the base (such as at the midpoint of the blade length or the like). The methods and systems described herein as performing both tests simultaneously significantly reduce the time required for blade fatigue testing, which increases throughput of a test facility. Additionally, the testing system may be mobile to allow it to be taken to a manufacturing facility rather than shipping the large blades significant distances.

Briefly, the blade support (or test stand) is not rigidly mounted to the ground or a test platform but is, instead, mounted such that it may pivot or translate in one or more directions (e.g., about or in one or more points or axes). An excitation input assembly is provided to provide the forcing functions or oscillating inputs to move the platform, and a base of an attached blade or test article, in one or more directions (e.g., to shake the base to oscillate the blade). The excitation input assembly includes one or more oscillating systems or actuators that provide the single or multi-axis excitation. These actuators typically are linked or placed in abutting contact with a driving member/assembly that, in turn, is attached to or placed in contact with the blade support.

In operation, the actuators cause the driving member/assembly (or a portion thereof) to be displaced a particular amount or distance, which causes the blade support to move in one or more directions. As a result, the base or root of the turbine blade moves in one or more directions, which causes the blade to oscillate allowing fatigue testing in one or more directions (e.g., in a flap wise direction, in an edge wise direction, in pitch, and so on).

The response of the system is determined by or is relative to the system inputs. Blades under loading will deform about a complex axis due to typical design and construction attributes. The input loading is typically referred to as flap and edge, but the response will be a combination of these directions and others (e.g., torsion). In the following description it is understood that the direction of the response is roughly aligned with the input loading, but it will deviate from any 'exact' local or global coordinate system. Hence, the terms flapwise and edgewise oscillation in a blade due to similar inputs may be considered at least somewhat of an approximation (e.g., two input sets of excitation forces may be generally orthogonal (e.g., transverse and in planes that are about 90 degrees apart (e.g., 70 to 110 degrees or the like) and the direction of the response in the blade may be substantially/generally orthogonal, too (e.g., in the edgewise and flapwise directions or the like)) and/or their may be other components such as twist-coupling phenomena (e.g., torsional movements of the blade) due to concurrent excitation forces in differing directions.

A number of oscillating systems may be used to provide the base excitation of the test article or wind turbine blade (also referred to herein as "blade"). In other words, the term "actuator" is intended to include nearly any device that may be used to provide displacement at a particular frequency or rate such as a hydraulic or other linear or rotary actuator, an electric motor, and so on. Generally, the oscillating systems may include one or more actuators or other devices for imparting forcing functions in one, two, or more degrees of freedom or directions in a controlled manner (e.g., at the edge and/or flap resonant frequencies of the test system). For example, the oscillating system may provide a first linear or rotary actuator to cause the driving member/assembly to move in a first direction (e.g., vertically to cause the base to move and oscillate the blade in the flapwise direction) and a second linear or rotary actuator to cause the driving member/assembly to move in a second direction (e.g., horizontally to cause the base to move and oscillate the blade in the edgewise direction). The actuators of the excitation input assembly may be operated by a control system with displacement signals provided at natural or other frequencies (e.g., constant amplitude sinusoidal displacement signals at the same or more typically at differing amplitudes to simulate in-use or a predefined loading condition).

FIG. 1 illustrates schematically a wind turbine blade testing system of one embodiment adapted to perform fatigue testing of a wind turbine blade 104 using base excitation. For example, the system 100 may be used to provide concurrent fatigue testing in one, two, three or more axes or degrees of freedom (e.g., concurrent or sequential testing in the flapwise and edgewise directions). The system 100 includes a test stand or blade support 110 for retaining a test article such as blade 104 in a cantilevered arrangement with the base or root end 106 of the blade 104 rigidly or semi-rigidly affixed to the blade support 110 and the blade 104 extending outward with its tip end 108 being unrestrained along its length or along the longitudinal axis, $axis_{blade}$. The blade 104 may be nearly any blade design with the test system 100 being particularly well suited for use with larger blades such as those in use in 1.5

Megawatt and larger wind turbines, e.g., 40 meter and larger blades being typical. The larger blades are more easily tested with the system 100 because edgewise testing is performed with an excitation input assembly 120 that is not mounted to the body of the blade 104 along its span or length but instead in contact with the blade support or test stand 110, which allows the system to handle large blade displacements (e.g., up to 6 meters or more with some larger blades that are oscillated at or near the flap resonance). The system is well suited for testing blades with large sensitivities to transverse displacements or rotations such as bend-twist coupled blades as the method is not restricted by geometric load effects from ground-plane referenced forcing loads.

The system 100 includes an excitation input assembly 120 for providing forcing functions or to cause displacement at selectable frequencies in one, two, or more directions (e.g., multi-axis inputs such as in the flapwise, edgewise, and pitch directions of the blade 104). The oscillating assembly 120 may take a number of forms to provide the forcing functions or oscillating inputs. For example, one or more oscillating actuators 124 may be provided to excite the blade support 110 to excite the base 106 of the blade 104 in a first direction, e.g., in the flapwise direction (e.g., transverse or orthogonal to a plane extending generally between the leading and trailing edge of the blade 104 and containing the longitudinal blade axis 109 or out of plane). In some cases, the actuator 124 may be also adapted to oscillate the blade support 110 to excite the base 106 of blade 104 in a second direction, e.g., the edgewise direction (e.g., in a direction transverse to the blade axis 109 or in the blade plane). The excitation input assembly 120 typically includes a drive assembly (not shown in FIG. 1) that is in contact with the blade support 110 (such as to a vertical face or surface of the support 110 or to a base/mounting structure of the support 110) and operation of the actuators 124 applies an oscillating force or load upon the blade support 110 causing it to move in one or more directions. Movement of the blade support 110 is shown with arrows 126, 128 with arrow 126 representing movement of the blade support 110 about a first axis and arrow 128 representing movement of the blade support 110 about a second axis (e.g., to cause the blade 104 to oscillate with two degrees of freedom such as generally in a flapwise direction and generally in an edgewise direction). The application of force by the actuators 124 typically will be lines or directions that are transverse and, in some cases, planes containing such forcing functions are orthogonal, although this is not required.

The actuators 124 are operated by a control system 130 to excite the base 106 of the blade 104 to move or oscillate as shown at 115 in a first direction (e.g., the flapwise direction by applying forces out of the rotor plane (e.g., orthogonal to the blade plane) and at or near the flap natural frequency of the test system 104). Concurrently (or during the same operating or test period), the actuators 124 are operated by the control system 130 to excite the base 106 of the blade to move or oscillate as shown at 117 in a second direction (e.g., the edgewise direction by applying forces in the rotor plane (e.g., parallel to or coplanar with the blade plane) and at or near the edge natural frequency of the test system 104). Typically, the flap and edge resonant frequencies differ such that edge and flap forcing functions use two differing frequencies, but, in some embodiments, these two frequencies may be substantially the same. The actuators 124 may be hydraulic or other types of actuators such as electric motors to provide the desired oscillations 115, 117.

The control system 130 includes a processor or feedback processor 132 running a controller or control module (e.g., a PID controller or the like) 134. Memory 136 is provided that stores test parameters and measured and/or determined test data. This stored data may include excitation frequencies for base excitation in one or more directions 138 and excitation strokes or displacements 139 with these values being used by controller 134 for use in timing the transmittal of corresponding displacement signals 160-164 to the oscillating assembly 120 to operate the actuators 124 (e.g., displacement signals to a flapwise actuator and to an edgewise actuator). The stored data may also include a tabulation or count of the number of load or fatigue cycles 140 that have been imparted during operation of the system 100 to fatigue test the blade 104. Yet further, the stored data may include loads or moments for the edge and flap 142, 144 such as may be measured by sensors 150, 152, such as strain gauges or as may be determined based on calibrations of accelerometers or other transducers. Although not shown, the control system 130 may further include software for displaying or outputting the data in memory 136 such as in table or graph form and for performing desired calculations such as determining moments 142, 144 from accelerometer output signals (e.g., signals 154 or the like).

Sensors 150, 152 are provided on the flap and edge portions of the blade 104 and output blade response/feedback signals 154 are processed by the feedback processor 132 for use in operating controller 134 to transmit displacement signals 160-164 to operate the actuators 124 of excitation input assembly 120 to maintain the loads applied to the blade 104 within a predefined test or load envelope (e.g., within predefined maximum loads/blade bending moments) and/or to maintain displacements of the blade 104 within a desired displacement envelope (e.g., within predefined maximum flapwise and edgewise displacements). For example, the signals 160-164 may have amplitudes that are set by the controller 134 in response to determinations by the processor 132 of the moments experienced by the blade in the edgewise and flapwise directions based on feedback signals 154 from sensors 150, 152. The signals 160-164 may be transmitted at the excitation frequencies 138 in phase or more typically with a variable phase offset (e.g., such as a 90 degree lag between the first direction displacement signal 160 and the second (or additional) direction displacement signal 164).

As will become clear, test or testing systems may be implemented to achieve a variety of goals. For example, some embodiments described herein address the desire to eliminate the need for specialized hydraulic equipment including pumps, hoses, and actuators while providing a test system that acts to oscillate a test article (e.g., wind turbine blade) in one or more directions. In some cases, the test system is mobile, and some embodiments may be thought of as directed toward a mobile oscillatory fatigue operator (MOFO) test system and associated testing methods. Exemplary MOFO test systems may use a motor or other actuator(s) to resonate a blade by oscillating the blade at its root or base, such as by "shaking the base" by applying an excitation displacement at a particular frequency to a blade support (or "reaction structure") upon which the root or base of the blade is mounted.

For example, the blade support may be pivotally mounted at its base such that the attached blade may be vertically displaced a particular displacement or through a stroke length at a test or driving frequency (e.g., near the blade's resonant frequency or the like) so as to resonate the blade in either a first or second direction (e.g., in either the flapwise or edgewise direction). The actuator (e.g., an electric motor) may include a flywheel system to rotate a link that is attached to a drive member or frame of an excitation input assembly, such as with a prismatic joint or the like, at a point spaced apart or distal to the blade support (e.g., a tip of the drive member or frame). The other end of the drive member or frame is connected to the blade support. During operation of the actuator, the drive member or frame's vertical deflection causes the member to rotate at its connection point to the actuator about a revolute joint or other mounting arrangement mounted to a test platform (or the ground). As the drive member or frame has its tip or end moved up and down, the portion of the drive member or frame attached to the blade platform applies a forcing function or excitation force/load to the blade platform that causes the blade to move or pivot back and forth about its base and shake the root or base of the attached blade.

Figure 2:
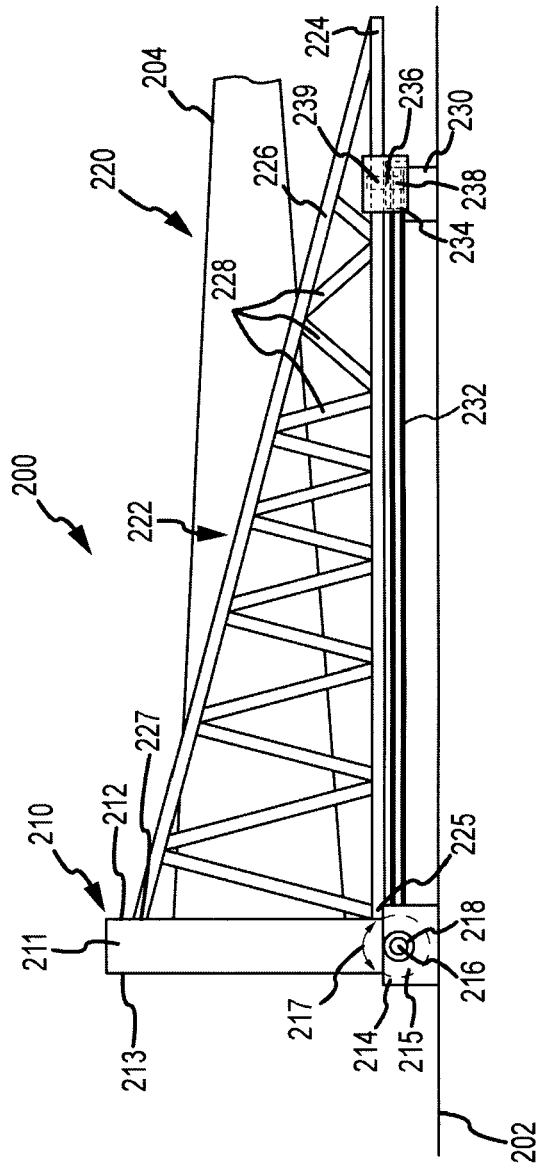
FIG. 2 is a side view of a blade test system adapted for oscillating a wind turbine blade via base excitation.

FIG. 2 illustrates a fatigue testing system 200 of one embodiment useful for single axis (or single degree of freedom) testing of an elongate test article such as a wind turbine blade 204. Generally, the system 200 includes a pivotal base support assembly 210 and an excitation input assembly 220 for shaking or exciting the support assembly to oscillate the wind turbine blade 204 (e.g., oscillate the blade 204 in the flapwise direction). The base support assembly 210 includes a body or reaction structure 211 that is pivotally supported along its base or lower edge 215 by a mounting member 214. Mounting member 214, in turn, is rigidly attached to the ground or a test platform 202 (e.g., a concrete pad or the like). The pivotal mounting may be achieved in a number of ways such as through the use of a rod or shaft 216 extending through (or out of the sides) of the reaction structure 211 that is supported at each end within the mounting member via bearings 218. The mounting member 214 may include two blocks (e.g., right and left ground mounts) to support the reaction structure 211 at each side, with each block including a bearing (or bearing assembly) 218 for receiving ends of the shaft 216. When a driving or excitation force or load is periodically applied to a mounting face 212 of the reaction structure 211 by excitation input assembly 220, the reaction structure pivots as shown at 217 about the shaft 216 in bearings 218.

The excitation input assembly 220 includes a drive frame or truss 222 that is shown arranged as a right triangle with a first or base drive element 224 and a second or upper drive element 226. The first and second drive elements 224, 226 are attached to the mounting face or surface 212 of the reaction structure 211 at ends 225, 227 and attached to each other at the other end. The drive elements 224, 226 are also structurally linked or interconnected via truss or joist members 228. An actuator mounting frame (or plate) 232 provides vertical support for an actuator (e.g., an electric motor or the like) 234 and to the drive frame 222. The actuator mounting frame 232 is attached at one end to the mounting member 214 and at the other end to a second mounting member 230, which is attached to the test platform or ground 202. The actuator 234 is position upon the actuator mounting frame 232 and linked to a pivot arm or bar 239, such as via a flywheel that when rotated causes the pivot arm or bar 239 to travel generally in a circular motion. The pivot arm or bar 239, in turn, is connected to a linkage or force transmission arm 236, and the transmission arm 236 is pivotally attached at 238 to the actuator mounting frame 232 and slidably attached at the other end to the base element 224 of the drive frame 222. Of course, other actuators may be used to vertically displace the frame 222 toward the end distal to the blade support 210, with the arrangement shown only intended as one useful example. In practice, two frames 222 may be utilized with one mounted on each side of the blade 204 so as to better distribute excitation input loads/forces, and, in such cases, the pivot arm or rod 239 may extend between the base members 224 to allow a single actuator 234 to be used (or two actuators may be used to drive the two frames 222).

During use of the system 200, a test article such as a blade 204 is mounted with its base or root rigidly attached to mounting face 212 of the reaction structure 211 (e.g., via an adapter plate or the like selected for the particular blade configuration and its mounting requirements). Operation of the actuator 234 (e.g., a drive motor driven by a controller as shown in FIG. 1) causes the end or tip of the frame 222 to be raised and lowered relative to the platform 202, and this cyclical vertical displacement causes the reaction structure 211 to pivot as shown at 217 about its base 215 and mounting point (e.g., shaft 216). Movement or excitation of the reaction structure 211, in turn, causes the blade 204 to be oscillated generally in the vertical direction (e.g., in the flapwise direction in the illustrated arrangement).

Figure 3:
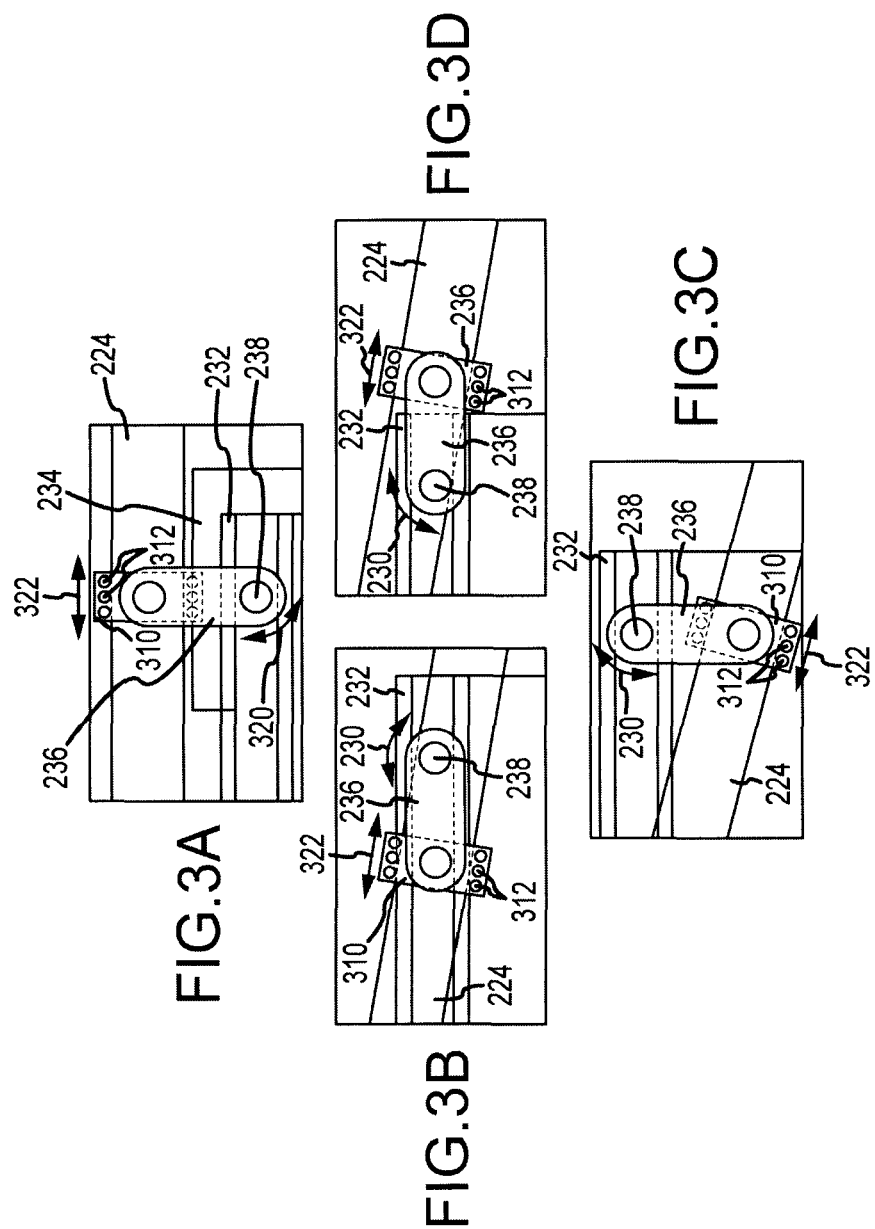
FIGS. 3A-3D illustrate detailed views of a linkage arrangement of the test system of FIG. 2 that is useful for connecting an actuator (e.g., a motor) to a drive frame or assembly.

FIGS. 3A-3D illustrate in more detail operation of the excitation input assembly 220 to input a vertical forcing function to cause the base or root of the blade 204 to oscillate in one direction (e.g., in the flapwise direction at or near the resonant frequency of the system). FIG. 3A shows the input assembly 220 in a starting or at rest position with the vertical linkage or force transmission arm 236 in a vertical position. As shown, the arm 236 is pivotally mounted at one end via pin 238 to actuator mounting frame 232. The arm 236 may be mounted at the other end using a linear or prismatic joint (e.g., a sliding joint with the axis of the joint coincident with the center line of the sliding link 310). To this end, the pivot arm or rod 239 is shown to be attached to the transmission arm 236 and also to follower carriage 310 that is fitted over or upon the base frame 224 so it may slide linearly along the frame element 224 as the linkage or transmission arm 236 rotates with movement of the pivot arm or rod 239. Bearing(s) 312 may be provided to facilitate movement of the follower carriage 310 upon the surfaces of the base element 224 of frame 222 as the actuator 234 moves the pivot arm 239 (e.g., an electric motor causes a flywheel attached to the pivot arm 239 to rotate or another actuation technique is applied to cause displacement of the arm 239).

FIG. 3B shows the input assembly 220 in a second position in which the pivot arm or rod 239 has been rotated counterclockwise about 90 degrees from its first or at rest position. This movement of the arm 239 causes the transmission arm 236 to pivot 320 about pin 238 on motor mounting frame 232. It also causes the follower carriage 310 to slide linearly along the base element 224 of frame 222 while it pulls the frame 222 downward to a second "lower" vertical position. The movement of the frame 222 (or its end distal to blade support 210) causes forces to be applied to the mounting face 212 (e.g., near its top at mounting location of upper element 226 of frame 222) and reaction structure 211 that make the reaction structure 211 pivot 217 a distance away from frame 222. Oscillating or excitation input continues in FIG. 3C with the pivot arm 239 being moved to a bottom vertical position placing the transmission arm 236 in a second vertical position with the follower carriage 310 below the actuator mounting frame 232. In this position, the frame 222 may be applying no force upon the reaction structure 211 or a tensile force pulling the structure 211 back toward its original position.

In FIG. 3D, the pivot arm 239 has been moved by the actuator 234 further in the counterclockwise direction (e.g., into a horizontal plane with the pivot pin 238), which may cause the frame 222 to apply a tensile force upon the mounting face 212 of the reaction structure 211 causing it to pivot 217 toward the frame 222. In FIG. 3A, the oscillation input cycle is completed with the frame 222 (and base element 224) as well as linkage or transmission arm 236 returned to the at rest position. During the movement of the frame 222 and interconnected reaction structure as shown in FIGS. 3A-3D, the attached blade 204 is also moved first up and second downward (or through a vertical displacement or through one excitation stroke). By repeating the movements shown in FIGS. 3A-3D, the base of the blade 204 is excited and the blade 204 oscillates to allow fatigue testing, e.g., fatigue testing in one direction at the input or operating frequency of the actuator 234.

The testing system 200 provides a number of advantages and features. The use of two input drive assemblies or frames 222 with the blade support assembly 210 provides a support stand for the blade 204. In some cases, the structure 211 may be relatively small and lightweight compared with existing test stands, without requiring large concrete blocks or weights (although counterweights may be used in some cases to counterbalance the weight of the blade 204 to reduce loads at the follower carriage 310 such as by mounting or attaching on face 213 of the structure 211). In other cases, the system 200 may be used to concurrently test two blades 204 by mounting a second blade of similar configuration on the face 213 (such as on an adapter plate provided on the structure 211). The frame 222 and blade support 210 may be adapted to provide proper support and balancing with only a single pair of frames 222 adjacent one of the two blades, and only one actuator (or actuator assembly with 1, 2, or more actuators) 234 may be used to excite or shake the base to oscillate the two attached blades 204. The frame 222 may be formed of steel or other metallic materials and be sized and/or shaped to provide a better stand or support for the blade 204. In one embodiment, for example, the frame 222 is sized such that the center of gravity of the blade 204 coincides with about the end of the base member 224 or tip of the frame 222 (where elements 224 and 226 mate), e.g., the length of the base element may be about 16 to 20 meters for a 40 meter blade.

The base elements 224 are elongate and selected to have a length between the surface 212 of reaction structure 211 and excitation input location (e.g., position of pivot arm 239 attachment) that provides a desired amount of leverage such that less force has to be provided by the motor or actuator 234 to pivot 217 the reaction structure 211 and supported blade 204 (e.g., to excite or shake the blade base or root). The testing system 200 also is relatively mobile and may be loaded upon a truck for transfer to blade manufacturing facilities and other blade locations, as the system 200 and its frame 222 (which may be considered a mobile fatigue testing stand) is self supporting in some embodiments and requires little anchoring to ground or a test platform (which may be a truck bed in some cases). In some embodiments, it may be desirable for the test system 200 to be adapted for variable amplitude testing, and this may be achieved by changing out the linkage or transmission arm 236 to provide a different displacement or stroke (or range of pivoting 217 of the structure 211). In other cases, variable amplitude testing is supported with a variable length link 236 (e.g., a link or arm that may have a length adjustable via a linear or other actuation device). A controller (such as controller of system 100 of FIG. 1) may be used to change the speed (or frequency) of the excitation (e.g., by changing the operational frequency of the actuator 234).

The system 200 may be used for fatigue testing in any single direction such as flapwise, edgewise, pitch, or other direction by adjusting the mounting orientation of the blade 204. Additionally, the system 200 may be used in conjunction with other excitation devices to provide dual or multi-axis resonance or fatigue testing, such as by mounting an excitation device upon the blade 204 to provide excitation or oscillation in a direction that differs from the direction of oscillation provided by system 200 (e.g., the system 200 may cause blade 200 to oscillate in the flapwise direction and an additional excitation device may be used to impart edgewise oscillation of the blade 204).

Figure 4:
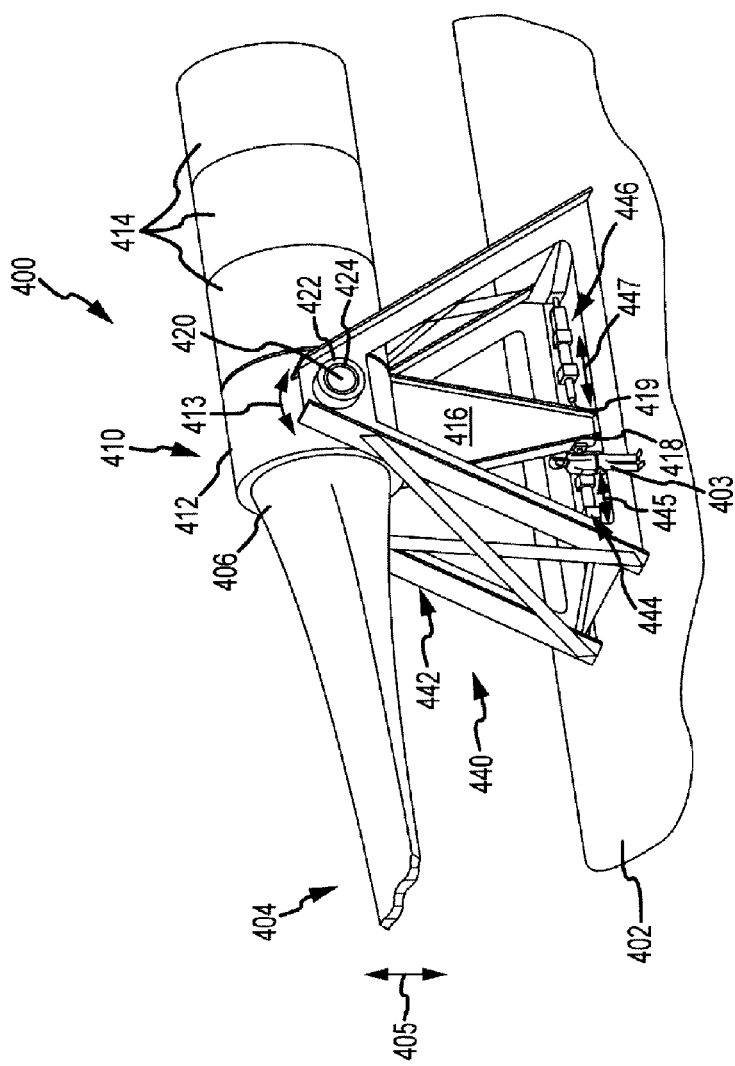
FIG. 4 illustrates a perspective side view of another embodiment of a blade fatigue testing system illustrating an alternative blade support arrangement and excitation input assembly.

FIG. 4 illustrates another embodiment of a blade testing system 400 adapted for more efficient fatigue testing of wind turbine blades 404 (e.g., in a flapwise direction as shown or in other directions). The system 400 represents a more compact design relative to system 200 as the blade support assembly 410 and excitation input assembly 440 are both positioned proximate to the position of the blade root or base 406. Further, the excitation input assembly 440 is adapted to position the blade 404 at a height that avoids interference with the ground or a test platform 402. Additionally, the system 400 more readily supports testing of two blades 404 as the counter weights 424 may readily be replaced with a second blade (e.g., a blade of similar design as blade 404).

As shown, the excitation input assembly 440 includes a structural or base frame 442 that is attached or mounted to a test platform or the ground 402. The specific design of base frame 442 is not limiting, but the base frame design may be chosen to properly elevate the blade base 406 to account for blade displacement (with height of the base typically being several to 10 or more meters as represented by height of test observer 403) and to also support the weight of the blade and cantilevered forces during testing. The base frame 442 physically supports the blade support assembly 410 such that it can pivot about the mounting axis (e.g., an axis of extending shafts or pins 420).

The blade support assembly 410 includes a hub 412 that is pivotally 413 mounted to the base frame 442, such as via pins/shafts 420 extending outward from each side of the hub 412. The hub 412 is configured for mounting of at least one blade 404 on one end (e.g., with an adapter plate provided within or on hub 412), with the blade base or root 406 being affixed to the hub 412, and, typically, the longitudinal axis of the blade 404 will extend transverse and/or substantially orthogonal to the pivot axis of the hub 412 (e.g., the axis of the shafts/pins 420). The blade 404 is cantilevered from the hub 412 such that when the hub 412 is pivoted or excited the blade 404 oscillates as shown at 405 in one direction (e.g., in the flapwise direction as shown or another direction depending on the mounting of the blade 404).

The hub 412 (and attached blades 404 and weights 414) are supported upon collar 422, which may be an integral portion of frame 442 or an added element, and the collar 422 includes bearings 424 to facilitate rotation or pivoting 413 of the hub 412 during use of system 400. The bearing design is not limiting and may take a number of forms such as a sleeve or shaft bearing (e.g., a solid Teflon® tube or the like). The hub 412 is also adapted for supporting a second blade opposite the first blade 404 or, alternatively, a set of counterweights 414 to counter balance the weight of the blade 404. In one embodiment, for example, the counterweights 414 may be weighted (e.g., concrete-filled) pipes that are chosen to match the blade weight, cantilevered forces, and forces developed during tests (e.g., a 70 meter blade may weigh 40,000 kg and the weights 414 may be 3 concrete-filled pipes weighing 50,000 kg each).

To facilitate oscillating of the hub 412 and the base 406 of blade 404, the blade support assembly 410 includes a fin (or reaction structure/element) 416 that extends outward from hub 412. The fin 416 may be planar member with sidewalls 418, 419 for receiving input or excitation forces, and the fin 416 may be generally planar as shown with a frustoconical or other shape. The fin 416 is arranged such that application of forces as shown at 445, 447 cause it to transmit forces to the hub 412 causing it to pivot 413 about pin/shafts 420 (e.g., a plane extending through the fin 416 is transverse to the axis of the pins/shafts 420 and may be parallel to or coincident with longitudinal axis of blade 404). The fin 416 in the embodiment 400 extends downward into the base frame 442 to provide a more compact and readily serviceable arrangement, but it may extend from an upper or other surface of the hub 412.

The system 400 includes an excitation input assembly 440 with a pair of actuators 444, 446 mounted to the base frame 442 and placed in abutting contact with sidewalls 418, 419 of fin 416. For example, 50-kip linear actuators may be used to input excitation or displacing forces at a desired frequency to cause the hub 412 to pivot/oscillate 413 and shake the base 406 to cause resonant or other oscillation 405 in the vertical direction (e.g., the blade 404 oscillates generally in the flapwise direction in the illustrated system 400). Again, the actuators 444, 446 may be controlled with a controller or control system (as shown in FIG. 1, for example) to adjust the amount of displacement/stroke 445, 447 and/or the speed/frequency of the excitation 413. In some embodiments, a single actuator may be used in the place of the two actuators 444, 446 (e.g., to push and/or pull on the fin 416 and/or on one of the sidewalls 418, 419). Note, the fin 416 may also be thought of as replacing the drive or input frame of FIG. 2 allowing relocation of the actuator(s) and provides a leverage arm for inputting forcing functions. The length or height of the fin 416 is chosen to provide a desired amount of leverage to the actuators 444, 446 to allow them to pivot 413 the hub 412 about pins/shafts 420 on bearing/bearing surface 424. As with other embodiments, dual-axis fatigue testing may be performed by adding or providing additional actuators, e.g., resonant actuators on the blade span to provide edgewise (or second direction) excitation concurrently with operation of actuators 444, 446.

Exemplary embodiments of system 400 enable the ability to test two blades at once, and, hence, the system 400 may be considered a double-sided MOFO design (or DMOFO design) may use a motor, hydraulic cylinders, or other actuators to create the oscillatory motion shown in FIG. 4 and resonate one or two blades at the same time in a single direction (e.g., edgewise, flapwise, or other direction). Dual-axis (e.g., flapwise and edgewise) excitation may also be performed, e.g., by adding a horizontal degree of freedom to the DMOFO design 400 by placing an actuator or excitation device on top of a turntable bearing or by using other bearing arrangements. In addition, the blade platform 410 may be used as a static test stand or as a static foundation by anchoring the counterweight to the ground/platform 402. As shown, each blade 404 is mounted to the rotating or rotatable hub 412. If desired, only one blade may be tested at a time as shown with a blade replaced by counterweights 414. The frame 442 and support assembly 410 is semi-mobile as it is a self-contained structure that is fastened to a foundation 402.

The DMOFO system 400 provides a number of desirable features and advantages. Two blades may be tested simultaneously on the same stand with a single set of hydraulics or other loading/actuating systems, which increases the throughput of a testing facility (e.g., doubles throughput). The bearing location is in-line with the pitch axis of the blade 404. Corresponding motion more accurately simulates the motion of blades in the field and reduces the moment of inertia of the system 400, thereby requiring less hydraulic or input excitation forces. In addition, the hub 412 supporting the pins/shafts 420 and bearings 424 may be less expensive to produce compared with existing test stands while providing increased structural efficiency. An actuator (e.g., hydraulics, electric drive, or the like) may be positioned underneath the bearings 424 and hub 412, which allows the actuators 444, 446 to be placed in a low, horizontal position that is easier to install and inspect than a vertical actuator. Further, the position of these actuators 444, 446 facilitates use of multiple, smaller actuators by placing them on either side of the lever arm or fin 416, which reduces the size of the actuators thus reducing the need for costly, large, custom actuators required in prior testing systems to fatigue test large blades (e.g., up to 40 meter or larger blades).

The anchoring system (e.g., base frame 442) is more compact and potentially less expensive than a very long truss-style frame (e.g., frame 222 of system 200). A ballast system (not shown) may be used for static testing, and the ballast system may be dual-purpose in that it may be used to rotationally strain the test stand for static testing, thereby reducing overall system cost. The mean angle of the test stand 442 can be easily changed for static and fatigue testing, thereby reducing the height of the test stand hub 412 and potentially resulting in a less expensive, shorter building of lower height. Again, the DMOFO uses base excitation to oscillate 405 the blade 404 (or blades 404). One set of hydraulic cylinders are located on a stationary reference frame 442, thereby reducing the installation time and allowing the system 400 to be test a wide range of blade lengths without installing specialized equipment for each size range of blades.

Figure 5:
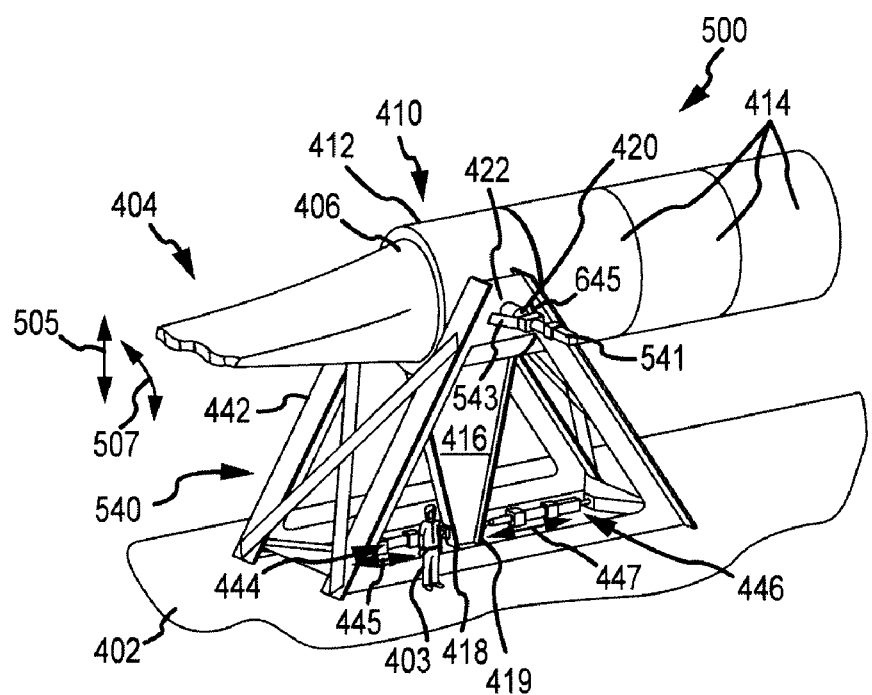
FIG. 5 illustrates a perspective side view of the testing system of FIG. 4 adapted for dual-axis fatigue testing (e.g., for imparting base excitation in at least two directions)
Figure 6:
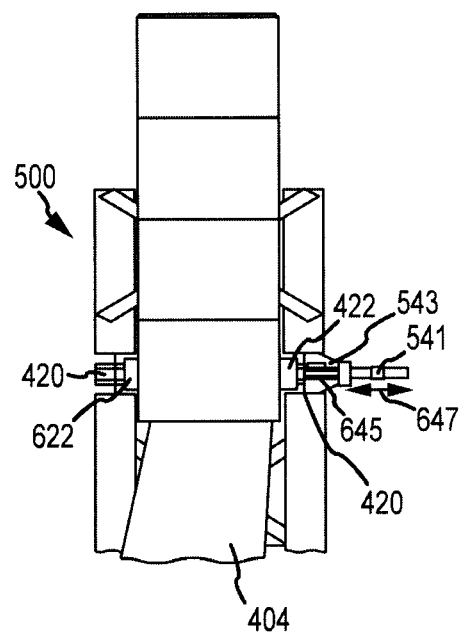
FIG. 6 is a top view of the testing system of FIG. 5 showing details of an actuator assembly for excitation of a blade base in a second direction (such as in an edgewise direction)

In many applications, it is desirable to perform dual-axis or multi-axis fatigue testing of wind rotor blades rather than sequentially testing in a single direction or degree of freedom. FIGS. 5 and 6 illustrate a multi-degree of freedom blade testing system 500 that utilizes the concept of base excitation. In contrast to the systems 200 and 400, though, the base excitation is in two or more directions of degrees of freedom so as to enable concurrent fatigue testing in multiple directions (e.g., oscillating a blade in the flapwise, edgewise, and/or pitch direction in a single testing period). The excitation may be resonant (e.g., excitation input at or near resonant frequencies of a blade in an edge direction and the flap direction) or be forced excitation at a different frequency or speed.

FIG. 5 illustrates blade-testing system 500 adapted for testing with two degrees of freedom testing of one or two blades 404 (e.g., dual-axis, base-excitation, blade testing). The system 500 generally builds upon the system 400 of FIG. 4 with modifications/additions to provide excitation or forcing in a second direction or degree of freedom. The system 400 was adapted for testing in a single direction such as the flapwise direction of a blade (as shown in FIG. 4). In contrast, the system 500 is adapted for fatigue testing in two directions that are transverse to each other and that may be substantially orthogonal (e.g., 70 to 110 degrees from each other) such as resonating a blade 404 in a first, generally vertical direction 505 and a second, generally horizontal direction. In this manner, for example, a blade 404 may be excited or shaken at its base 406, which is attached to a hub 412 in a blade support assembly 410, to concurrently (e.g., within a single test period but, in some cases, at offset phases) oscillate in a flapwise direction 505 and in an edgewise direction 507.

As shown, the excitation input assembly 540 of system 500 includes actuators 444, 446 for applying forces as shown at 445, 447 to lever arm or fin 416 to pivot 413 the hub 412 about pins/shafts 420, and this causes blade base 406 to be moved or oscillated to cause the blade 404 to oscillate in a first direction 505 (e.g., generally vertical or in the flapwise direction with the blade mounting as shown in FIGS. 5 and 6). Additionally, the system 500 includes an additional actuator(s) 541 to provide dual or second axis testing of the blade 404. The actuator 541 may be a linear actuator that is attached to the base frame 442 proximate to the pins/shafts 420 and collar 422 (with a second pin/shaft 420 supported by collar 622, which includes a bearing(s) to facilitate sliding and rotating motion of pin/shaft 420).

During operation of the actuator 541, a force transmission element or shaft 645 of the actuator 541 abuts or contacts the shaft or pin 420, which is rigidly connected to hub 420. The force transmission element 645 may apply a force or cause linear displacement 647 of the shaft/pin 420 and, therefore, the hub 420 in a direction that is transverse (and, in some cases, substantially orthogonal) to the movements 413 of the hub 412 in response to inputs 445, 447 of actuators 444, 446. The input 647 of actuator 541 may be controlled to provide resonant or forced excitation 507 of the blade 404 in a second degree of freedom or direction (e.g., in an edgewise direction) via excitation of the blade base or root 406. The oscillating 505, 507 may be concurrent to provide dual-axis fatigue testing of the blade 404 (and, in some cases, a second blade replacing weights 414) using base excitation. The hub 412 in system 500 is mounted on base frame 442 for two degrees of freedom movement in that it can pivot 413 and also slide horizontally in response to linear input 647, which allows the blade 404 to be excited at its base in two directions or degrees of freedom The system 500 may be considered a universal MOFO design. Like the DMOFO system 400, the UMOFO system 500 may be used as a single-axis fatigue test stand, a static test stand, and/or as a rigid foundation by anchoring the counterweight 414 or lever arm 416 to a fixed reference frame. The UMOFO system 500 may also use base excitation for dual-axis fatigue testing as shown in FIGS. 5 and 6. The UMOFO system 500 uses base excitation, thereby avoiding the use, and associated challenges associated with use of, high pressure hydraulic systems and large moving masses placed on flexible, fragile blades 404. In the UMOFO system 500, the hydraulic cylinders or other actuators may be located or mounted on the stationary reference frame 442, thereby increasing facility throughput of blades by reducing the system complexity, installation and tuning time, and facilitating testing of a wide range of blade lengths without installing different resonant excitation testing equipment for each range of blades 404.

The UMOFO system 500 is adapted to allow translational motion 507 of the blade 404 in the horizontal (or generally horizontal) direction and rotational motion 505 of the blade 404 in the vertical (or generally vertical) direction. It may be desirable, though, to provide differing arrangements of a UMOFO system, such as to address concerns with bearing service life due to pivoting and sliding of the hub 412 (or shaking the base 406 of blade 404) that will generate significantly high forces (due to the weight of the system components such as blade 404 and weights 414 as well as of hub 412) causing wear of bearings and bearing/contact surface in system 500 (as well as in systems 200, 400).

For example, another dual-axis, base excitation testing system 700 is shown for use in fatigue testing a wind turbine blade 704. The UMOFO system 700 shows a bearing arrangement that differs from that shown in system 500 for handling forces created by base excitation in two or more directions, but the UMOFO system 700 is also useful for oscillating a base 706 of a blade 704 to generate oscillation in two directions 705, 707 (e.g., flapwise and edgewise directions). As shown, the system 700 includes a blade support assembly 710 with a hub 712 for receiving and supporting a base or root 706 of a test article 704, and counterweights 716 are attached to the other side of the hub 712 to counterbalance the blade 704. The hub 712 is mounted onto a test platform or foundation 702 via pedestal 714. A collar 721 extends from the hub 712 and a shaft extends within the collar 721 and is received supported within the pedestal 714. A bearing or bearing surface 726 is provided about or in contact with the shaft 724 to facilitate rotate or pivoting 748 if the hub 712 during operation of the system 700. The bearing 726 may be a thrust or other type of bearing to support rotary motion of shaft 724. The collar 721 may also include bearings 723 such as bearing pucks to support an amount of vertical displacement or sliding 752 of the shaft 724, which causes excitation of base 706 and oscillation 705 of blade 704.

The system 700 further includes an excitation input assembly 740 that includes a lever or torque arm (or input/drive frame) 742 that is affixed to one or more of the counterweights 716. The assembly 740 also includes an actuator 746 that is mounted on a support frame 744 (which is attached to platform 702), with the actuator 746 acting upon the torque arm 742 to apply a linear forcing function 747 (e.g., a linear displacement of the arm 742 at a particular input frequency). This input excitation is transmitted by the arm or frame 742 to the counterweights 716 and interconnected hub 712 causing the hub 712 to rotate or oscillate 748 a small amount about a vertical axis of the shaft 724. To provide dual-axis excitation, a second actuator 750 is mounted on the hub 712 to be in abutting contact with the shaft (or a second shaft/pin) 724 extending from hub 712. Displacements or forcing functions 752 are applied by the actuator 750 on the hub 712 via the shaft 724, and a collar 720 is used to support one or more bearings (e.g., bearing pucks) 722 to support sliding motion. The use of puck bearings 722, 723 are easily replaceable and allow the shaft 724 to be a large diameter. The displacements 752 are in a direction that differs from the direction of the first displacement 748, and the two directions may be in transverse or even orthogonal planes (e.g., horizontal and vertical planes). During operation of the system 700, the base 706 is shaken or oscillated in two directions causing concurrent oscillation of the blade 704 as shown at 705, 707.

The above examples describe translating test systems that oscillate blades in two axes (e.g., dual-axis testing) by rotating the test stand or reaction structure supporting the blade base in one direction and translating the test stand or reaction structure in a transverse direction. The translating motion may wear out the bearings relatively rapidly during fatigue testing because only a small portion of the bearing supports the translating or sliding motion. In addition, the bearing life in the translating test system may further be reduced because the bearings are in the load path of the oscillating horizontal fatigue loads and the horizontal static testing loads. Additionally, some translating test systems may not have mechanical leverage in the translating direction requiring use of relatively large and expensive linear actuators.

Figure 8:
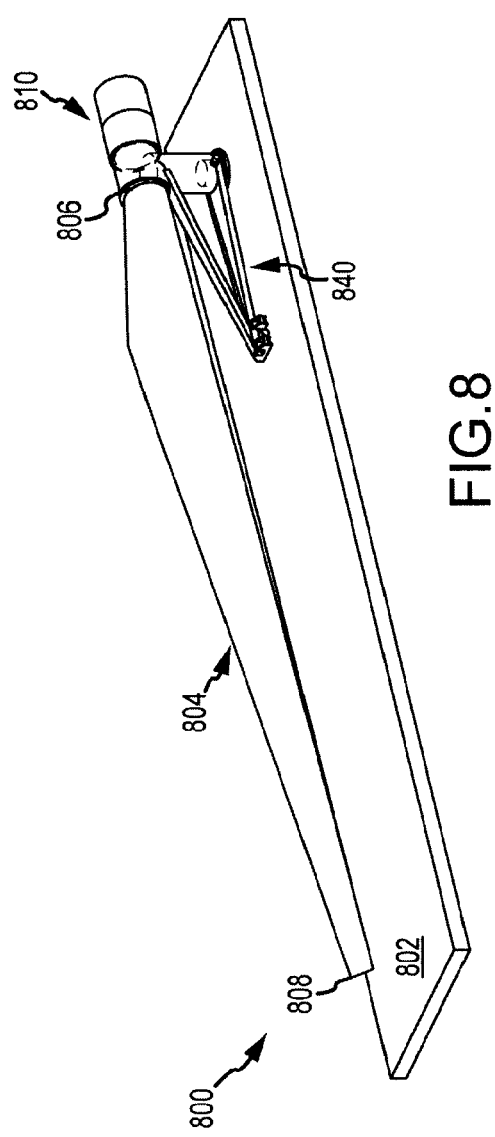
FIG. 8 is a side perspective view of another embodiment of a dual-axis fatigue testing system.
Figure 9:
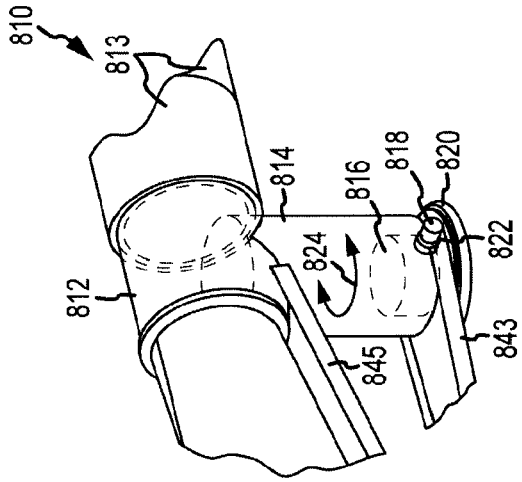
FIGS. 9 and 10 are views of the testing system of FIG. 8 illustrating support and excitation input details or features.
Figure 10:
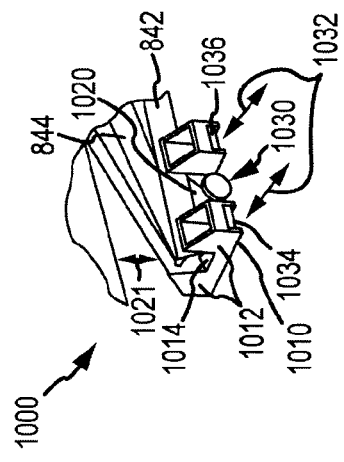

With these issues in mind, an additional embodiment of a UMOFO test system 800 is shown in FIGS. 8-10. The system 800 is a rotation-based fatigue testing system for wind turbine blades 804, with one being tested and counterbalanced with weights 813 while other uses may test two blades concurrently with a blade replacing the weights 813. The system 800 is adapted to extend the bearing life and reduce actuator costs. The rotational UMOFO system 800 replaces the translational motion with a rotational motion that is conducive to longer bearing life due to the elimination of the translational motions and by isolating the main bearings from the oscillating and static test loads. In addition, exemplary embodiments such as system 800 use a long lever arm that parallels the blade axis. The long lever arm (e.g., see frame with base and upper arms/members 843, 845) provides mechanical advantage for horizontal and vertical testing (e.g., two direction excitation) reducing the required actuator capacities. The long lever arm can extend to the rear of the blade support assembly or to the front as shown in FIGS. 8 and 9. Extending the arm to the front along the blade 804 reduces the radial loads on both sets of rotary bearings and the foundation during static and fatigue testing, and results in a shorter overall length of the UMOFO system 800.

Referring to FIG. 8, the rotational UMOFO system 800 includes a blade support assembly 810 mounted upon a test platform or foundation 802. A test article or blade 804 is attached at its base 806 to the support assembly 810 such that its tip 808 is supported in a cantilevered manner relative to the assembly 810. The system 800 includes an excitation input assembly 840 that is adapted to rotate the support assembly 840 and base 806 in two degrees of freedom or two directions such as vertically (or cause the support 810 to rock back and forth) and horizontally (or cause the assembly 810 to pivot about its vertical central axis).

Rotation about two transverse axes is achieved as shown in FIGS. 9 and 10 with system 800. In FIG. 9, additional details of the blade support assembly 810 are provided with the assembly 810 including a hub 812 onto which the blade base 806 is mounted as well as the counterweights 813. The hub 812 is affixed to a support member 814 (e.g., a cylindrical support element or the like), which is pivotally mounted via rotational bearing 820 to the testing platform or foundation 802 such that the support member 814 may rotate 824 about its vertical or central axis (not shown). A stub 816 may extend up from the bearing surface 820 and the support member 804 may be positioned upon this pivotal stub 816. The stub 816 may include horizontal supports or pins/shafts 818 extending out from each side and through the walls of support member 814. A pair of rotational bearings 822 may be provided at the area of mating between the pins/shafts 818 and the support member 814 such that the support member or reaction structure 814 may pivot in a second direction (e.g., in a plane that is transverse to the pivoting or rotation 824 such as a generally vertical plane whereas rotation 824 is in a generally horizontal plane). By causing these two rotational movements of the support member 814 and attached hub 812 the base 806 of blade 804 is caused to oscillate in two directions (e.g., in flapwise and edgewise directions or the like).

The system 800 also includes the excitation input assembly 840 with includes an input or drive member or frame formed (in this example) with a base arm 843 and an upper arm 845 that are attached at a first end to the support member 814 (e.g., at a contact surface or face of member 814 similar to surface 212 of structure 211 in FIG. 2) and are connected to each other at a second end distal to the support member 814. Pivoting of the support member 814 about two axes is achieved by positioning the base member 843 upon a mobile trolley 1000 that rides upon wheels, casters, or bearings 1034, 1036 on platform 802 as shown at 1032. The trolley 1000 supports a first actuator 1020 that is arranged to act as a vertical actuator and applies an excitation or forcing function to the base member 843 and upper member 845, whereby the tips 842, 844 of the members 843, 845 are moved up and down in a vertical channel 1014 between sidewalls or vertical members 1012 of trolley 1000. This vertical movement 1021 causes the support member 814 to pivot about shafts/pins 818 and oscillates the base 806 of blade in the vertical direction.

To provide dual-axis oscillation, a second actuator 1030 is mounted upon the platform 802 and placed in contact with the trolley 1000 to cause the trolley to move along a small arc or curved path on platform 802 as shown at 1032. This movement in the horizontal plane (or plane of the surface of platform 802) is translated via base member 843 and upper member 845 of the excitation input assembly 840 to the support member 814, which causes the support member 814 to rotate or pivot about its vertical axis on the bearing 820. The hub 812 moves with the support member 814 in this second direction, which shakes or excites the base 806 causing oscillation of the blade 804 in a second direction (e.g., in an edgewise or other direction).

In this manner, the rotational UMOFO system 800 implements a trolley 1000 to guide the arm assembly (e.g., members 843, 845) simultaneously in the vertical and horizontal directions. In alternative embodiments, two actuators may be implemented without a trolley to provide this rotational movement in two directions or to provide movement of the blade support in two degrees of freedom. In such an arrangement, two force members may be oriented orthogonally or at other angles to control the motion of the arm assembly (e.g., members 843, 845). Such a configuration reduces part count by eliminating the need for the trolley and its components, but it may require a more complex control algorithm because the actuator displacements are coupled, requiring motion in each for a single vertical or horizontal motion.

Figure 7:
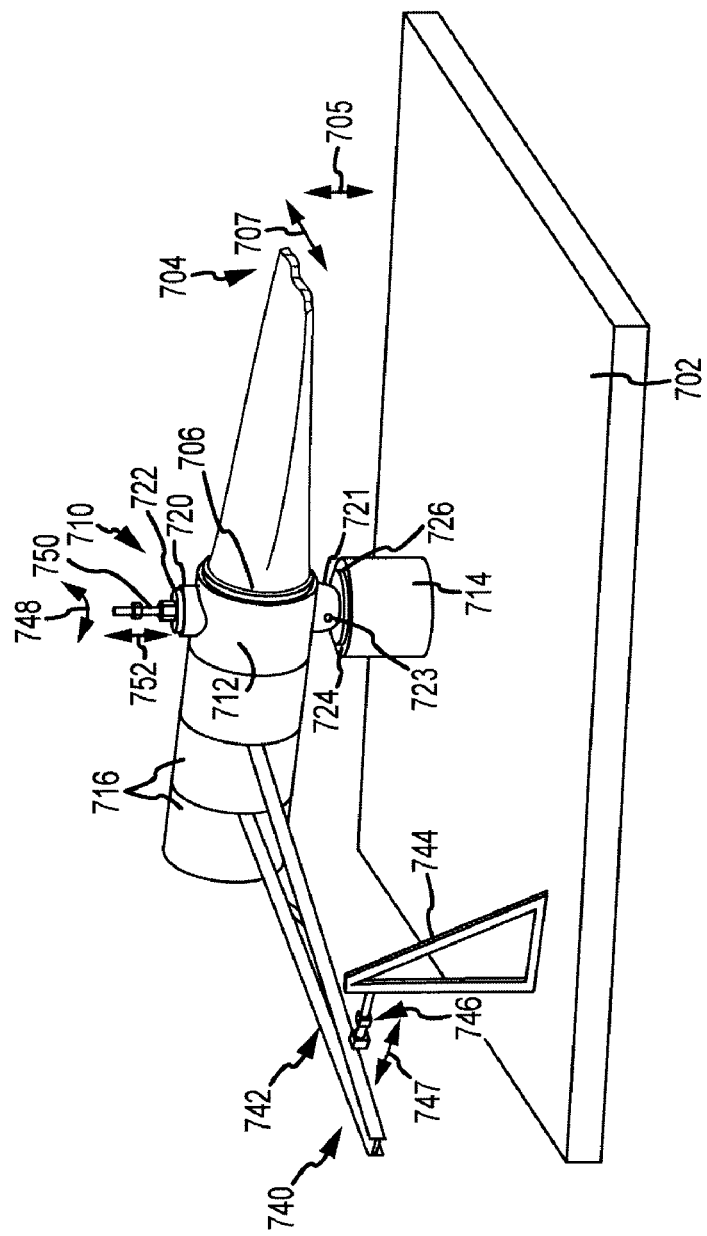
FIG. 7 illustrates another test system adapted for fatigue testing of a wind turbine blade in two directions (e.g., adapted for dual-axis excitation of a support assembly used to support a base or root of a blade or other elongate test article)

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include modifications, permutations, additions, and sub-combinations to the exemplary aspects and embodiments discussed above as are within their true spirit and scope. For example, the system 700 of FIG. 7 may be modified for use as a single axis or direction testing system. In such an embodiment, the actuator 750, collar 720, and bearing 722 (as well as a thrust bearing in collar 722 if provided for rotary motion). A single slew or similar bearing may be provided as bearing 726 at the base of the blade support 710. The blade 704 may be loaded for fatigue testing in a variety of directions such as either a flapwise direction (e.g., making the system 700 a sideways MOFO) or edgewise with motion 707 occurring in the oscillating blade 704.

Additionally, the testing systems may be augmented with additional actuators linked to a test article to excite a blade in an additional direction (e.g., the systems described may be used for first and/or second directions and another actuator may be provided to achieve dual-axis or multi-axis oscillation of a blade). A number of oscillating systems may be used to provide the concurrent or dual-axis excitation of the test article or wind turbine blade (with "blade" being used from hereon for ease of explanation). Generally, the oscillating systems may include one or more actuators or other devices for imparting both the flap and the edge forcing functions in a controlled manner (e.g., at the edge and flap resonant frequencies of the test system).

For example, the additional actuators or oscillating systems may provide one or more flapwise actuators and one or more edgewise actuators that are attached at the same or differing locations or stations along the length of the blade and are operated by a control system with displacement signals provided at natural frequencies (e.g., constant amplitude sinusoidal displacement signals at the same or more typically at differing amplitudes to simulate in-use or a predefined loading condition). These actuators may be provided, but are not limited to, via an augmented Universal Resonant Excitation (UREX) system such as by using the two flapwise actuators of a typical UREX system and adding an edgewise actuator or edge mounted UREX to provide the edge forcing function. Other hardware embodiments may include multiple flapwise and edgewise actuators at multiple distinct spanwise blade stations. In other implementations, the blade is excited in the flapwise direction using a Blade Resonance Excitation (BREX) system, which is described in U.S. Patent Application Pub. No. 2006/0037402, which is incorporated herein by reference in its entirety. In such an implementation, the blade may be concurrently excited in the edgewise direction using an Edge Resonance Excitation (EREX) system that may be BREX system applied to a blade to provide a forcing function in edgewise direction with or without modification. In other applications, the oscillating system utilizes a single actuator, such as a BREX-type system, to provide both forcing functions. This may be achieved, for example, by providing a displacement signal at an oscillating frequency composed of two distinct frequencies, e.g., a flap carrier signal with a riding edge frequency or the like.

In some cases, it has been recognized that it may be desirable to reduce the size and complexity of the excitation input assembly and/or the blade support assembly. For example, the wind turbine blade testing systems described above generally have utilized the actuators of the excitation input assembly to not only excite or displace the test article or blade but also to return the test article or blade to its original or "at rest" position. However, this may require actuators that are relatively large in capacity and/or in size, which can be undesirable for a number of reasons including added capital and maintenance costs, size requirements, and the like.

One technique for reducing the size of the actuators is to provide a mechanism to provide a restoring or returning force that acts to place the test article or blade back into the original or at rest position. Such a restoring mechanism may be passive in that it does not require power to operate or require control signals or the like to properly operate. To this end, some embodiments of the test systems described herein are modified to include a restoring spring element (which may include one or more springs or spring-like components) that is configured and/or positioned within the test system to have an at rest position that urges the test system and a mounted blade to an original or at rest position (e.g., a position of a turbine blade prior to operation of the excitation input assembly or imparting excitation forces with an actuator).

Such a test system may be provided, for example, by modifying the test system 400 shown in FIGS. 4-6 to include a restoring spring element or elements. In one such embodiment, one of the actuators 444 or 446 is replaced with a spring element such as a coil spring, a rod, a pipe, or the like fabricated from metal, a metal composite, or other materials such as fiberglass or the like. When remaining actuator moves in a first direction, the spring element is compressed, and when the force is removed the spring element attempts to return to its original or at rest configuration (e.g., return to an original, non-compressed length and shape). When the remaining actuator moves in a second, opposite direction, the spring element is stretched, and when the excitation or displacing force is removed the spring element again attempts to return to its original or at rest configuration. Both of these functions or characteristics of the restoring spring element act to provide a restoring or returning force, which does not have to be provided by an actuator. This allows smaller and, typically, fewer actuators to be used in the test system 400. Similarly, in embodiments as shown in system 800, a restoring spring element in the form of a torsional spring may be utilized to provide a restoring or returning force such as by modification of column support 814 or mounting of an additional spring component contacting this or another portion of the system 800.

Another issue or concern with some test systems is that large bearings may have to be used to allow relative motion between the blade root and the rigid, pivotally mounted base support structure. For example, the test system 200 includes large bearings 218, test system 400 includes bearings 424, and system 700 includes bearings 722, 723. There are a number of issues with the use of such bearings including high cost, short life due to fatigue of the rolling or sliding elements, and introducing slop or backlash into the test system. In addition, as mentioned above, the test systems using bearings for pivoting a rigid test stand, base support, or mounting hub to which the base of the test article is attached typically used very large and energy hungry actuators to accelerate the kinematic motions of the test stand and test article. The concept of a restoring spring element was discussed above for providing restoring forces that may reduce the need for actuators or actuator size and capacity. Further, it has now been recognized that it may be beneficial to provide wind turbine blade test systems with blade supports that include one or more spring elements to not only provide a restoring force or functionality but to also provide the pivotal mounting functionality for which the bearings were provided in some test systems.

Briefly, the following discussion describes enhanced base excitation test systems (BETS) or wind turbine blade test systems that provide an alternative supporting structure for the test articles or blades. The alternative support structure or blade support assembly (or blade support) includes one or more restoring spring elements positioned between the base or root of the blade and a test stand. The test stand in these embodiments is not pivotally mounted but is, instead, rigidly mounted to or affixed to a testing platform or foundation. The restoring spring elements (or assembly) may be used to replace the bearings described in the systems of FIGS. 1-10 yet the use of a restoring spring element in the blade support assembly allows for the relative motion desired to excite the blade base or root motion.

A blade excitation assembly is again provided with one or more actuators, which may be hydraulic or another type of actuator system, may be positioned to abut the spring element or another portion of the blade support assembly coupled to the spring element, such as a blade mounting face or plate used to receive the blade base or root. The actuators may be positioned at varying angles and locations to abut the spring element(s) or an interconnected blade mounting component to cause excitation of the blade base in one, two, or more degrees of freedom as discussed above (e.g., to cause flapwise, edgewise, and/or other excitation of a test article). The excitation assembly may operate similarly to the assemblies described above to excite the blade by moving or exciting the base, such as with the control system 130 shown in FIG. 1 to provide inputs/control signals for included actuators. The spring element(s) may be adjusted or configured to provide desirable levels or magnitudes of stiffness in each direction or degree of freedom effected by a test (such as a predefined stiffness or spring constant in the flapwise, edgewise, torsional, and/or other degrees of freedom).

For example, spring elements of different size, shape, material, and the like may be used with differing blade or test articles to provide desired restoring and pivoting/exciting performance. In some cases, the test system may be designed to test a blade near a natural frequency of the entire system, and the spring element(s) is selected to have characteristics such that the natural frequency of the test system with the blade installed on the blade support assembly is relatively close to the resonant frequency of the tested blade to provide adequate bending and/or stressing of the blade. In some embodiments, the restoring spring element or assembly includes a primary spring element that functions to physically support a test article or blade on a test stand and to provide the majority or a large percentage of the restoring or spring forces used to allow the blade to pivot at its base during excitation and also to return the blade to its at rest or original position. Further, though, the restoring spring element or assembly includes one or more tuning spring elements that are provided to allow the stiffness, spring constant, and other characteristics of the restoring spring element or assembly to be tuned to allow the test system to operate at or closer to a resonant frequency that is desired for the blade and/or to reduce actuator forces used to obtain a desired level of excitation and reduce or control energy consumption.

Hence, embodiments of a wind turbine blade testing system or BETS according to this description uses a restoring spring element to pivotally mount or support a base or root of an elongate test article such as a wind turbine blade, and the restoring spring element is "tunable" in that it may be provided a particular spring constant (or stiffness) through selection of one or more primary spring elements and also by addition of one or more resonance-tuning spring elements (which may be positioned proximate to the primary spring element(s) such as about the periphery of the primary spring element between the blade mounting plate and the test stand). The tunable aspect of the restoring spring element or assembly allows for dual axis testing by modifications of the spring constant of the spring element in one or more directions. For example, a tuning spring may be added to increase the stiffness or change the spring constant in the edgewise direction while another tuning spring may be added to increase the stiffness or the spring constant in the flapwise direction, and these added tuning springs or spring elements may have differing configurations to provide different increases/changes in the spring constant in these two excitation directions.

Figure 11:
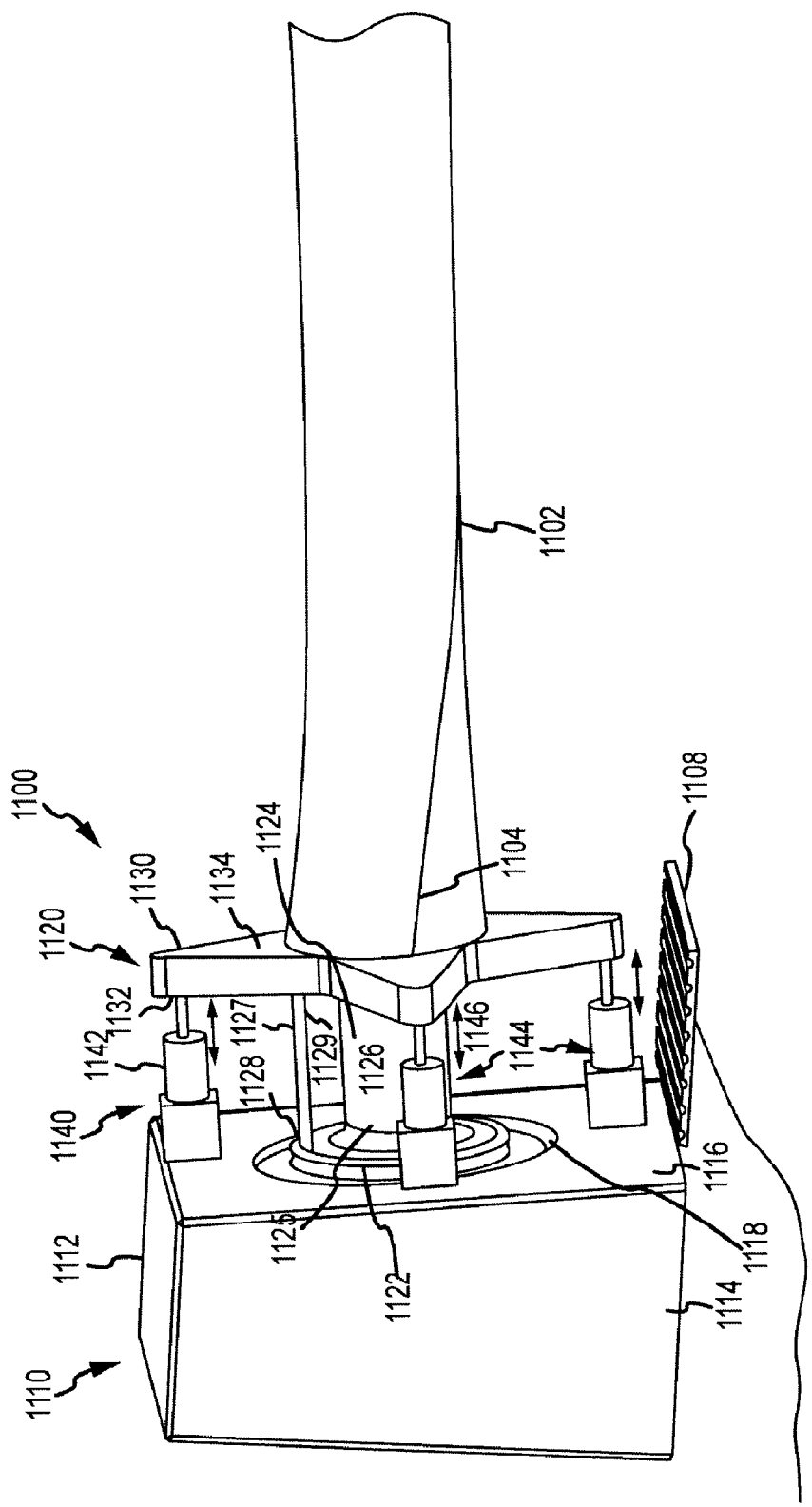
FIG. 11 illustrates a wind turbine blade testing system or base excitation test system (BETS) utilizing a blade support structure with a restoring spring element or assembly for pivotally mounting a test article such as turbine blade.

FIG. 11 illustrates a wind turbine test system or BETS 1100 that utilizes spring-based mounting of a test article such as blade 1102 to pivotally mount the base or root 1104 of the blade 1102. The spring-based mounting also provides a restoring force to allow smaller actuators to be used and provides a tunable aspect that allows the resonant or natural frequency of the system 1100 during excitation to be matched to or selected to suit the resonant frequency of the blade 1102. The system 1100 includes a blade support or blade support assembly 1110 and an excitation input assembly 1140, which may be adapted as described above for the other test systems to excite the base 1104 of blade to provide dual-axis or multi-axis excitation or testing to the blade (e.g., to provide excitation in the flapwise, edgewise, and torsional directions or degrees of freedom).

As shown, the blade support assembly 1110 includes a test stand or blade support structure 1112 that is attached to and or supported by a test platform 1108. In contrast to the prior systems, the system 1100 uses a rigid or fixed test stand 1112 that does not pivot but is instead mounted to or supported at a base or lower end 1114 by the platform 1108. The test stand 1112 may take a conventional blade test stand form such as including one or more large concrete blocks or structures to provide ballast to support cantilevered mounting of a wind turbine blade 1102. On a vertical face or side 1116 of the test stand 1112, a mounting hub or flange 1118 is provided that may be used to receive and support a restoring spring element or spring element assembly 1120. The mounting flange 1118 may be of the type typically used to receive a root or base 1104 of a blade 1102 so as to allow existing or conventional test stands 1112 to be used in the system 1100 (although, of course, this is not a requirement for implementing the system 1100).

The blade support assembly 1110 further includes a restoring spring assembly or element 1120 to facilitate pivotal mounting of the base or root 1104 of the blade 1102 in the test system 1100. Generally, the spring element 1120 functions to provide a mounting surface for the base 1104, to attach the blade 1102 to the test stand 1112, and to allow the base 1104 to be excited by the excitation input assembly 1140 (e.g., by providing pivotal mounting of the base 1104 and providing a mechanism to tune the frequency of the system 1100). To this end, the illustrates spring element 1120 includes a base or base plate 1122 that is adapted for mounting to the mounting flange 1118 of the test stand 1112, and, in some cases, the base 1122 is circular in shape with a plurality of mounting holes for receiving studs, bolts, or other mounting fasteners to rigidly couple or attach the spring element 1120 at a first end to the test stand 1112.

The spring element 1120 also includes a primary spring element 1124 that extends outward from the base 1122 and is attached at a first end 1125 to the base 1122. The spring element 1124 provides the primary spring force or restoring force and also allows the base 1104 to be moved or excited during testing (e.g., pivotal mounting). The spring element 1124 may take many forms to practice the system 1100 to provide these functions with the element 1124 of FIG. 11 being shown as having a generally cylindrical body or form. For example, the spring element 1124 may be a solid cylinder formed of a metal such as a steel, a metal composite or compound, or other material (such as fiberglass or the like), with the material being chosen to provide a desired strength to support the blade 1102 and also a desired spring constant and/or stiffness. In other embodiments, the spring element 1124 may take the form of a hollow cylinder (or pipe) while other embodiments may use differing cross sectional shapes to provide the desired functions of the element 1124. For example, the spring element may take the form of a rod with a rectangular cross section, an oval or elliptical cross section, or the like (solid or at least partially hollow body). In other cases, the spring element may be a channel member (e.g., a C-channel), an I-beam, or the like to provide a desired resonance or other characteristic in one or more excitation direction.

At a second end 1126 (distal to the first end 1125), the primary spring element 1124 is attached to or coupled with a blade mounting face or plate 1130 with the end 1126 abutting a first or inner side 1132 of the plate 1130. The blade mounting face 1130 is shown to support the base 1104 of the blade 1102 with the base 1104 being attached (e.g., rigidly affixed with fasteners as to a convention turbine hub with a plurality of fasteners) to a second or outer side 1134 of the plate 1130. The thickness and shape of the blade mounting plate 1130 may be varied to implement the system 1100 with the plate 1130 shown for example to include four arms (e.g., to take on a 4-pointed star pattern) that provides locations on the side 1132 for application of excitation forces or provides mating surfaces with actuators or other portions of the excitation input assembly 1140. In one embodiment, the plate 1130 is formed of metal such as from a steel plate with a thickness of at least about 2 inches. As shown, the spring element 1124 may have an elongate body with a longitudinal axis that generally coincides with a longitudinal axis of the blade 1102 (or nearly so with the two axes being parallel in this case).

To provide tuning of the spring element/assembly 1120, the spring element 1120 may include one or more additional or tuning springs or members 1127. In the illustrates example of system 1100, a single tuning spring 1127 is attached at a first end 1128 to the base and at a second end 1129 to the inner side 1132 of the blade mounting plate 1130. The tuning spring 1127 may take the form of a pipe or rod with a length that substantially matches the primary spring element but with a much smaller diameter such that the primary spring element 1124 provides a majority or even nearly all of the restoring force, supporting stiffness, and other functionality of the spring element 1120. For example, the primary spring element 1124 may provide 80 to 90 percent or more of the spring function (e.g., 95 to 99 percent or more in some cases of the spring constant and/or stiffness used to support a blade 1102) while the spring 1127 is included to adjust the spring constant in a particular direction to achieve a desired resonance frequency in an excitation direction such that the system frequency more closely matches resonant frequency of the blade 1102 in that direction.

In some cases, the primary spring element 1124 may be a solid shaft or cylindrical member with a diameter of 1 to 2 feet or more while the tuning element 1127 may be a solid shaft or hollow pipe-like member with a diameter of less than about 3 inches. As shown, the tuning spring 1127 may be used to increase the stiffness of the spring element 1120 in the flapwise direction while other embodiments may use one or more elements 1127 to increase stiffness in the edgewise direction (solely or concurrently with increases in the flapwise direction) and/or torsional direction. Only one tuning spring member 1127 is shown in FIG. 11, but more typically two or more spring elements 1127 may be used of like or differing configurations (e.g., differing diameters, materials, cross sectional shapes, and the like) to achieve a more accurate tuning of the system 1100.

The system 1100 further includes an excitation input assembly 1140 that may include one or more actuators and a control system that function to excite the base or root 1104 of blade 1102 by applying forces to the blade mounting plate 1130. Hence, the blade mounting plate 1130 may also be thought of as an excitation input member that is attached to springs 1124, 1127 that act to vertically support the plate 1130 and also return it to an original or at rest position (e.g., a home position when excitation forces or inputs are removed). As shown, the excitation input assembly 1140 includes a plurality of actuators 1142, 1144, 1146 (with a fourth hidden from view behind the spring element 1124) that may be operated in a cyclic manner as discussed above by a control system (such as system 130) to provide multi-axis texting or, in some cases, dual axis testing.

As shown, a pair of actuators 1142, 1144 are positioned on opposite sides of the primary spring element 1124 such as on a vertical plane passing through the center of the element 1124 or the like to apply push-pull excitation forces to the side 1132 of the blade mounting plate 1130 (e.g., to an upper and a lower arm of the plate 1130) to provide flapwise excitation of the blade 1102 via excitation of base 1104. A pair of actuators 1146 (with the other actuator not shown) may be positioned on opposite sides of the primary spring element 1124 such as on a horizontal plane passing through the center of the element 1124 to apply push-pull excitation forces to the inner side 1132 of the mounting plate 1130 (e.g., input forces applied to side arms of plate 1130). The actuators 1142, 1144, 1146 may be attached to the vertical face or side 1116 of the test stand 1112 and extend outward to abut the inner side of the mounting plate 1130. As discussed above, the actuators 1142, 1144, 1146 may be relatively small in size and/or capacity to achieve a desired level or magnitude of excitation when compared to test systems that do not employ a restoring spring assembly 1120 as the primary spring element 1124 and tuning springs 1127 act to apply a restoring force to the blade 1102 that does not have to be provided by the actuator devices.

In some cases, it may be useful to provide differing configurations for the excitation input assembly such as to reduce the number of actuators, mount the actuators in different locations (such as on the ground or another support rather than the test stand 1112), and/or to take advantage of the weight of the blade and gravity to cause blade movement/excitation. For example, FIG. 12 illustrates another BETS 1200 that may be used to provide fatigue testing of an elongate test article such as the wind turbine blade 1102. The BETS 1200 includes an excitation input assembly 1240 that differs from the assembly 1140 in that the two flapwise excitation actuators 1142, 1144 have been removed and are replaced with a single actuator 1244.

The flapwise (or vertical direction) actuator 1244 is shown mounted to or supported by the test platform 1108 in a location beneath or adjacent the blade mounting plate 1130. The actuator 1244 applies an input or excitation force to push the plate 1130 and attached base 1104 vertically upward to excite the blade 1102. The restoring spring assembly 1220 functions to resist this movement and to return the plate 1130 and base 1104 to an at rest or original/pre-excitation location or orientation. In this case, gravity will act to cause the blade 1102 to move lower vertically and typically overshoot the original or at rest position when excitation forces provided by the actuator 1244 are removed. Side-to-side or edgewise actuators 1146 again act on the plate 1130 or its side arms to cause excitation with push-pull forces to provide edgewise excitation of the base 1104. The actuators 1146 are shown to be mounted to the side 1116 of the test stand, but, in other embodiments (not shown), the actuators may be mounted to the test platform or ground 1108 or another support structure and apply input forces as shown to the inner side of the plate 1130 and/or to the outer side of the plate 1130. In some cases, the side or edgewise actuators 1146 will apply the excitation force or input to the edge, as is the case with actuator 1244, such as to side arms of plate 1130 or directly to the primary spring element 1124 near the end 1126 or the like. In such cases, the actuator or actuators 1146 may be mounted on the ground or on a support structure positioned adjacent and to the side of the spring element 1124. Additional actuators may be provided as discussed above to provide excitation in a torsional direction or degree of freedom.

As discussed above, many arrangements and configurations may be utilized for the one or more additional or tuning spring members of the restoring spring assembly 1220 to tune the resonance or other characteristics of the system 1200. As shown, in FIGS. 12 and 13, the restoring spring assembly 1220 includes a single upper or flapwise tuning spring 1127 as shown in FIG. 11, such as a solid rod or shaft with a first diameter. In contrast, though, the restoring spring assembly 1220 includes a plurality of side or edgewise tuning springs 1227, 1327 spaced apart from the primary spring element 1124 and extending part ways about the periphery or circumference of the element 1124. As shown, the tuning springs 1227, 1327 are also solid shafts or rods with a second diameter that is smaller than the first diameter of the tuning spring 1127. In the example system 1200, five tuning springs 1227 are provided on one side of the primary spring element 1127 and five tuning springs 1327 are provided on another side of the spring element 1124 (opposite the springs 1227). These springs 1227, 1327 change the spring constant at least in the edgewise direction such as by making the restoring spring assembly 1220 stiffer in the horizontal plane.

Again, the springs 1227, 1327 are shown with circular cross sectional shapes but other shapes (solid or at least partially hollow) may be used such ovals, ellipses, triangular, rectangular and the like and in other cases, a single member may be used in the place of the sets of springs such as a single solid, arced member replacing the sets of springs. In other cases, more conventional coil-type springs may be adequate to provide finer tuning of the system 1200 and its resonant frequencies. Also, the spacing from the surfaces or sides of the primary spring element 1124 may be varied to practice the system 1200, with one embodiment providing a spacing in the range of 3 to 6 inches or more and another embodiment positioning the tuning springs 1127, 1227, and/or 1327 relatively close such as 1 to 4 inches or more. In the illustrated embodiments, the tuning springs are typically positioned at the same spacing from the primary spring element 1124 such as positioned in a ring or circle extending about the element 1124 whereas in other cases the spacing may vary amongst the tuning springs with some being more closely positioned and others spaced further apart to achieve desired tuning of the system 1200.

Figure 14:
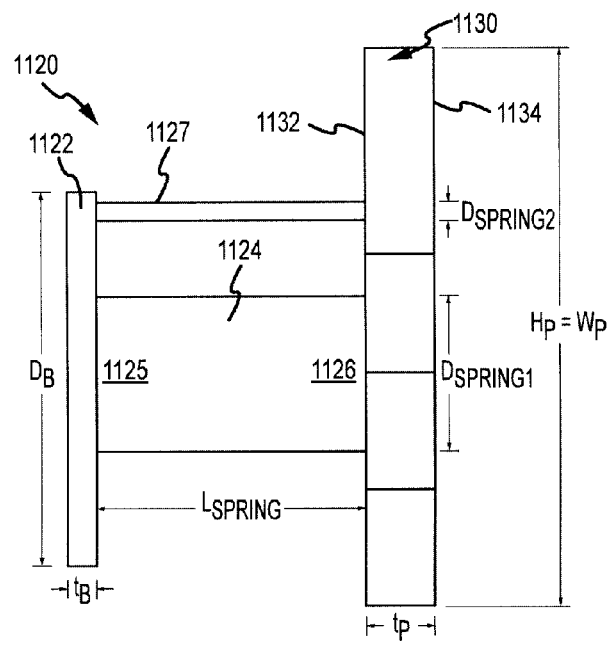
FIG. 14 illustrates a side view of the restoring spring assembly of FIG. 11.

FIG. 14 illustrates the restoring spring assembly (or "dog bone" as it may generally take this appearance) 1120 of the system 1100 in more detail. The assembly 1120 includes a base 1122 that is adapted for mounting to the test stand 1112, and, to this end, it may have a diameter, $D_B$, suited for mounting on wind turbine hubs as test stands often are adapted to receive blade roots or bases. The base 1122 may also have a thickness, $t_B$, such as 0.5 to 3 inches when steel or metal plate, chosen to provide structural integrity and support connection of the end 1125, such as by welding or the like, of the primary spring element 1124. The base 1122 is shown to be circular in shape, but it may take other shapes such as rectangular.

The primary spring element 1124 extends outward from a first end 1125 that abuts the base 1122 to a second end 1126 that is coupled to or abuts the blade mounting plate 1130 at inner surface 1132. The spring element 1124 may have a length, $L_{spring}$, and diameter, $D_{spring1}$, that are selected to provide a desired stiffness and/or spring constant and will vary depending on a number of factors such as whether the element 1124 is solid or hollow, what material is used for the element 1124, and what the length and weight of a supported blade is for a test run. In one embodiment, the spring element 1124 has a length, $L_{spring}$, in the range of 1.5 to 6 feet and a diameter, $D_{spring1}$, of 0.75 to 2.5 feet with the body formed with a solid cross section of metal such as steel.

In this example, the tuning spring(s) 1127 has an identical or similar length, $L_{spring}$, but a much smaller diameter, $D_{spring2}$, such as 4 inches or less in most cases. This is the case because the tuning spring 1127 is provided to tune or make minor adjustments or corrections in the stiffness of the assembly 1120 in one or more excitation directions to provide a desired overall system resonance for a test system 1100. In some embodiments, the tuning spring 1127 may be inserted or provided in the assembly 1120 after a blade 1102 has been attached to the mounting plate 1130 and resonance or other characteristics can be more accurately determined (such as by running short excitation runs). A testing process or operating procedure may include steps of running a planned excitation or fatigue testing for a limited time period, determining whether system resonance is matched adequately to the blade's resonant frequency, and, if not, adding one or more tuning springs 1127 prior to performing further initial or tuning steps. Once the system 1100 is properly tuned, the more lengthy or full multi- or dual-axis testing may proceed.

The blade mounting plate 1130 has four arms for facilitating receipt on the inner or first surface/side 1132 of actuating or input forces. The plate 1130 has a thickness, $t_P$, such as 2 to 4 inches or more of metal or steel plate, chosen to provide structural integrity and strength when a large wind turbine blade is mounted on the outer or second surface/side 1134. The plate 1130 also has a height and width, $H_P$ and $W_P$, that is selected to be larger than a diameter of the base or root 1104 of a blade 1102 (shown in FIG. 11) to facilitate mounting of the root 1104 on side 1134. Generally, though, the plate 1130 does not contribute to the stiffness or spring constant of the assembly 1120 but is more intended to provide a mounting/support surface for the blade 1102 and force-input surfaces for an excitation input assembly.

Figures 15, 16:
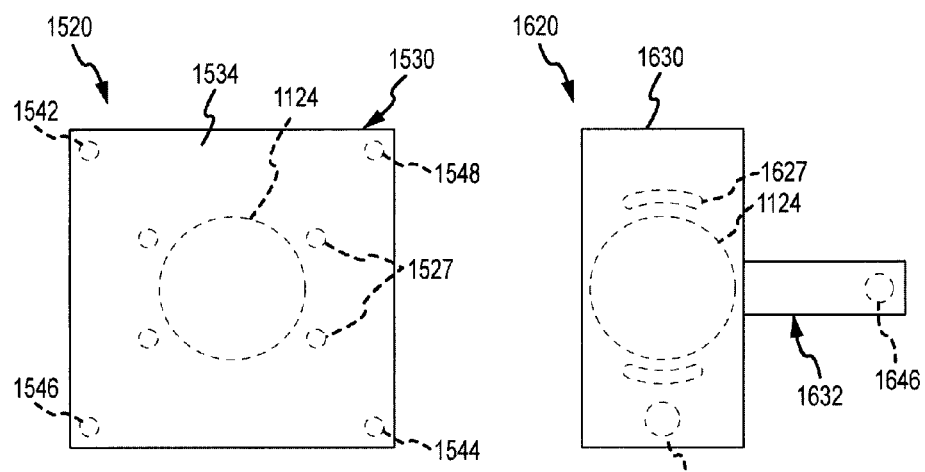
FIGS. 15 and 16 show end views of restoring spring assemblies that may be used in place of the spring assembly of FIGS. 11-14 in BETS described herein.

In other embodiments of test systems, the restoring spring assembly may take other forms than shown in FIGS. 11-14. For example, FIG. 15 illustrates an end view (e.g., from the blade side) of a restoring spring assembly 1520. In this assembly, the primary spring element 1124 is retained, but, as shown, a set of tuning springs 1527 is provided that includes four circular cross section rods or shafts. The tuning springs 1527 are positioned with two on each horizontal side of the element 1124, as may be desirable to increase stiffness or change a spring constant of the assembly 1520 in the edgewise direction, for example. The assembly 1520 also differs in that the blade mounting plate 1530 replaces the four-arm configuration with a rectangular or square shape or configuration with the spring element 1124 having it central, longitudinal axis extending through a center of the plate 1530 (and, typically, coinciding with a blade that may be mounted upon surface 1534, with the mounting components/fasteners for the blade not being shown in FIG. 15 but being similar to that found on a typical test stand 1112). With the use of the square plate 1530, actuators 1542, 1544, 1546, 1548 of an excitation input assembly may be positioned to contact an inner surface or side of the plate 1530 proximate to the four corners. In other cases, though, one or more of the actuators may apply inputs to the edge of the plate 1530 as shown in FIG. 12.

In FIG. 16, an end view (or blade-side view) is provided of another restoring spring assembly 1620. This assembly 1620 is configured with a main rectangular plate or body 1630 and a side plate, wing, or arm 1632. During use, a test article or blade may be mounted to the side or surface shown of the main plate 1630. The restoring spring assembly 1620 also may include one or more tuning springs 1627 proximate to the primary spring element 1124, which abuts the inner or first side of the main plate 1630 as with other restoring spring assemblies. In this example, two tuning springs 1627 are provided and positioned on upper and lower sides of spring element 1124 to provide stiffening or spring constant modification mainly in the flapwise direction.

The springs 1627 also do not have a simple circular cross section, but, instead, the springs 1627 are shown to have bodies with arcuate and/or elliptical cross sections that arch about the periphery of a portion of the spring element 1124. The springs 1627 are useful for demonstrating that the tuning spring members of the restoring spring assemblies described herein may take a wide variety of forms with numerous cross sections to provide the tuning function desirable in many test systems (e.g., to allow a single primary spring element design to be used with a range of blades, which may vary in their resonant frequency even within a single blade design/line due to manufacturing and other variances). An excitation input assembly may be used to apply input or excitation forces in a number of locations on the restoring spring assembly. As shown, an actuator 1642 applies an flapwise or vertical excitation force to the lower portion of the main plate 1630 with contact on the inner or first side, and an actuator 1646 applies an edgewise or horizontal excitation force to the side plate or wing 1632. Single actuators may be used for each direction due to the resilient characteristics of the primary spring element 1124 and tuning spring members 1627 that act to return the assembly 1620 and an attached blade to an original or at rest orientation or position (which is shown in this case in FIG. 16).

Figure 17:
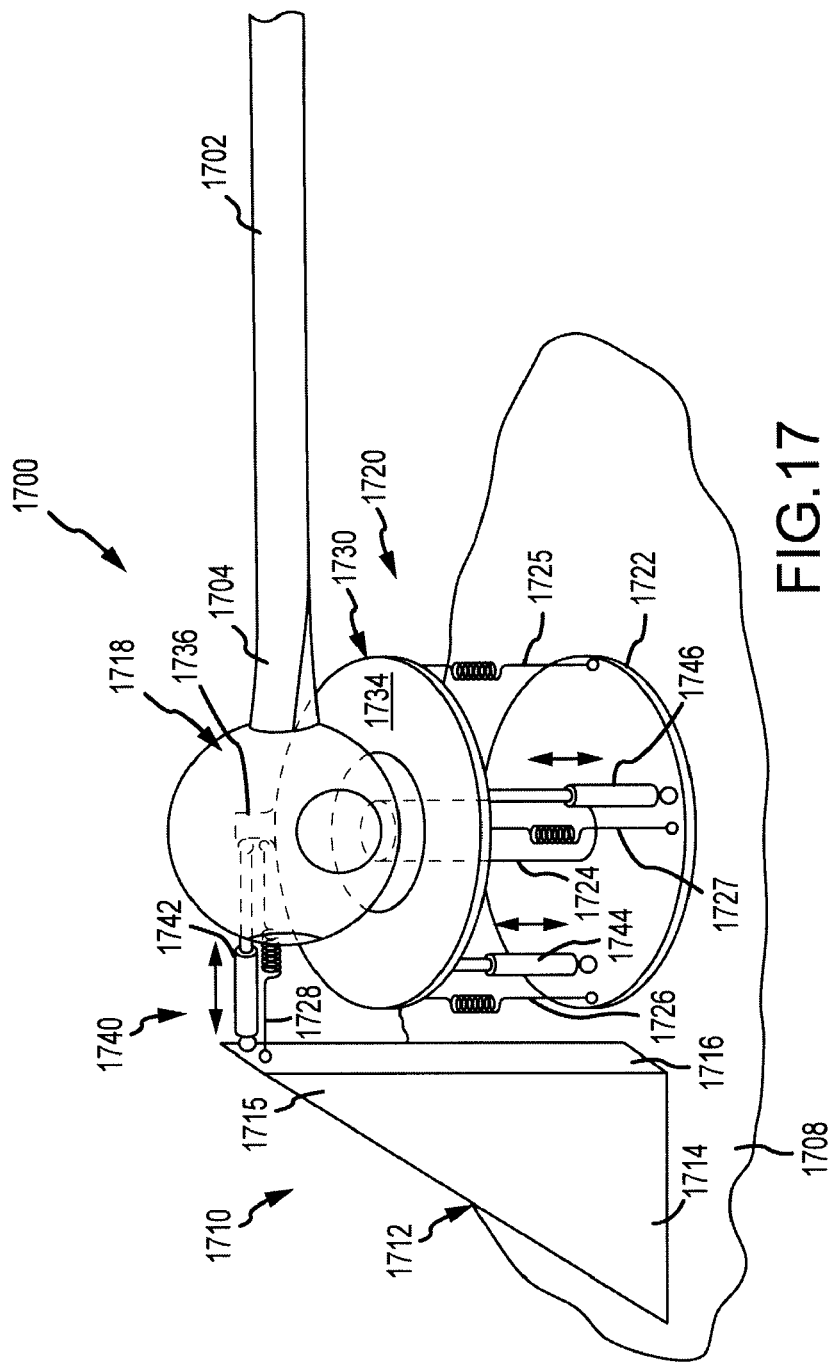
FIG. 17 illustrates a BETS embodiment with a vertical orientation.

FIG. 17 illustrates a BETS 1700 arranged with a vertical orientation of the restoring spring assembly 1720, and, particularly, with the primary spring element 1724 arranged or positioned with its longitudinal axis extending vertically or substantially vertically. BETS 1700 also includes a hub 1718 from a wind turbine, e.g., as may be used to support a blade 1702 at its base/root 1704 during use on a nacelle. The vertical BETS 1700 may provide a number of advantages. The vertical BETS 1700 facilitates hub testing (fatigue testing of a blade supported by its hub), which is more representative of conditions experienced in the field or in use, e.g., base stiffness and support conditions are more closely duplicated that may effect fatigue of the blade 1702. Additionally, it likely will be easier to properly design the dog bone or restoring spring assembly 1720 for the vertical BETS 1700 as the spring components may be loaded more in compression and tension and not subjected to shear forces resulting from gravity and the cantilevered mounting of a blade as is the case with horizontally mounted assemblies. The vertical BETS 1700 may also make it easier to adjust edge or edgewise stiffness to achieve desired base excitation of a blade 1702. For example, it may be easier to design a mechanism to adjust the edge stiffness provided by the restoring spring assembly 1720 resulting in a broader range of possible edge stiffnesses.

In the illustrated embodiment, the system 1700 includes a support assembly 1710, a restoring spring assembly 1720, and an excitation input assembly 1740. The support assembly 1710 includes a vertical restraint or test stand 1712 position upon and/or mounted to a test platform 1708 at a lower end or base 1714. In this non-limiting example, the restraint 1712 is triangular in shape with a mounting, vertical surface or side 1716 adjacent the restoring spring assembly 1720, and portions of the restoring spring assembly 1720 and input assembly 1740 are coupled to the vertical mounting surface 1716 near the upper end or top 1715 of the restraint 1712.

The restoring spring assembly 1720 is vertically arranged and includes a base plate 1722 is attached to or supported by the test platform/foundation 1708. Extending vertically (or at least partially vertically) from the base 1722 is a primary spring element 1724. The assembly 1720 also includes a blade mounting plate 1730, and the spring element 1724 mates at one end to the inner or first side of 1732 of the blade mounting plate 1730 and at a second end to the base plate 1722. The support structure 1710 (or the restoring spring assembly 1720) further includes a hub 1718 that is mounted to the outer surface or side 1734 of the blade mounting plate 1730, and the hub 1718 is chosen to be the hub or a similar hub as to what may be used during field use of the blade 1702. The blade base 1704 is attached to the hub 1718 in a conventional manner. By including the hub 1718, the testing with system 1700 provides more accurate or realistic testing of the blade 1702 as it accounts for the stiffness and/or other characteristics of the hub and of the base 1704 when it is attached to a hub 1718.

The restoring spring assembly 1720 may also include one or more tuning springs or tuning spring members such as to adjust edge, pitch/torsion, and/or flap stiffness. As shown, the restoring spring assembly 1720 includes a pair of tuning spring members 1725, 1726 that act to adjust stiffness and/or the spring constant of the assembly 1720 in the flap or flapwise direction. The spring members 1725, 1726 are depicted as coil springs but many other spring or resilient members may be used to adjust stiffness such as solid metal or other material rods and the like. The restoring spring assembly 1720 also includes a tuning spring member 1727 positioned to adjust or tune stiffness of the assembly 1720 in the pitch direction (e.g., offset from the longitudinal axis of the blade 1702 or the like). The spring members 1725, 1726, 1727 each are shown to extend between the base 1722 and the blade mounting plate 1730 in a vertical manner and are positioned about the periphery of the base 1722 and plate 1730 (but may be positioned nearer to or farther away from the primary spring element 1724 to provide desired tuning to the spring or other characteristics of the restoring spring assembly 1720).

Further, the restoring spring assembly 1720 includes a tuning spring member 1728 that extends from the vertical restraint 1712 to a wing or arm 1736 extending outward from a side or edge of the blade mounting plate 1730. The tuning spring member 1728 is again shown generally or schematically as any spring member and may take many forms to practice the system 1700 such as a rod, a tube, a coil spring, or the like. The tuning spring member 1728 is provided and positioned so as to allow adjustment or tuning of the stiffness or spring constant of the restoring spring assembly 1720 (and hence the system 1700) in the edge or edgewise direction. As discussed earlier, more or fewer tuning springs or spring members may be utilized to achieve a desired result, and, typically, the primary spring element 1724 is selected and configured to provide a significant portion of the forces to return the hub 1718 and attached blade base 1704 back to an at rest or pre-excitation position and to achieve a desired system resonant frequency.

The system 1700 includes an excitation input assembly 1740 which may include mechanisms for imparting excitation forces or displacements of the restoring spring assembly 1720 (which provides pivotal mounting of the base 1704 of the blade 1702) and may also include a control system for operating these mechanisms (such as control system 130 of FIG. 1). As shown, for example, a single actuator is provided to excite the base 1704 in each of three directions or axes to provide multi-axis testing of the blade 1702. Specifically, an edge actuator 1742 is provided that is mounted to the vertical side 1716 of restraint 1712 and extends out to the arm or wing 1736 of the blade mounting plate 1730, and the edge actuator 1742 is selectively operable to provide excitation of the base 1704 in the horizontal or edgewise direction. A flap actuator 1744 is provided that extends between the base 1722 of the restoring spring assembly 1720 and the inner or first surface 1732 of the blade mounting plate 1730. The flap actuator 1744 is operable to excite the base 1704 in the flapwise or vertical direction. In the system 1700, a pitch actuator 1746 is provided that extends between the base 1722 and the first surface 1732 of the blade mounting plate 1730. The pitch actuator 1746 is operable to excite the blade base 1704 in a pitch or torsional direction. Only one actuator is shown for each direction, but, in some embodiments, two or more actuators are provided in each direction (such as to provide push-pull actuation) while other embodiments may not include one or more of the actuators shown in system 1700.

Figure 18:
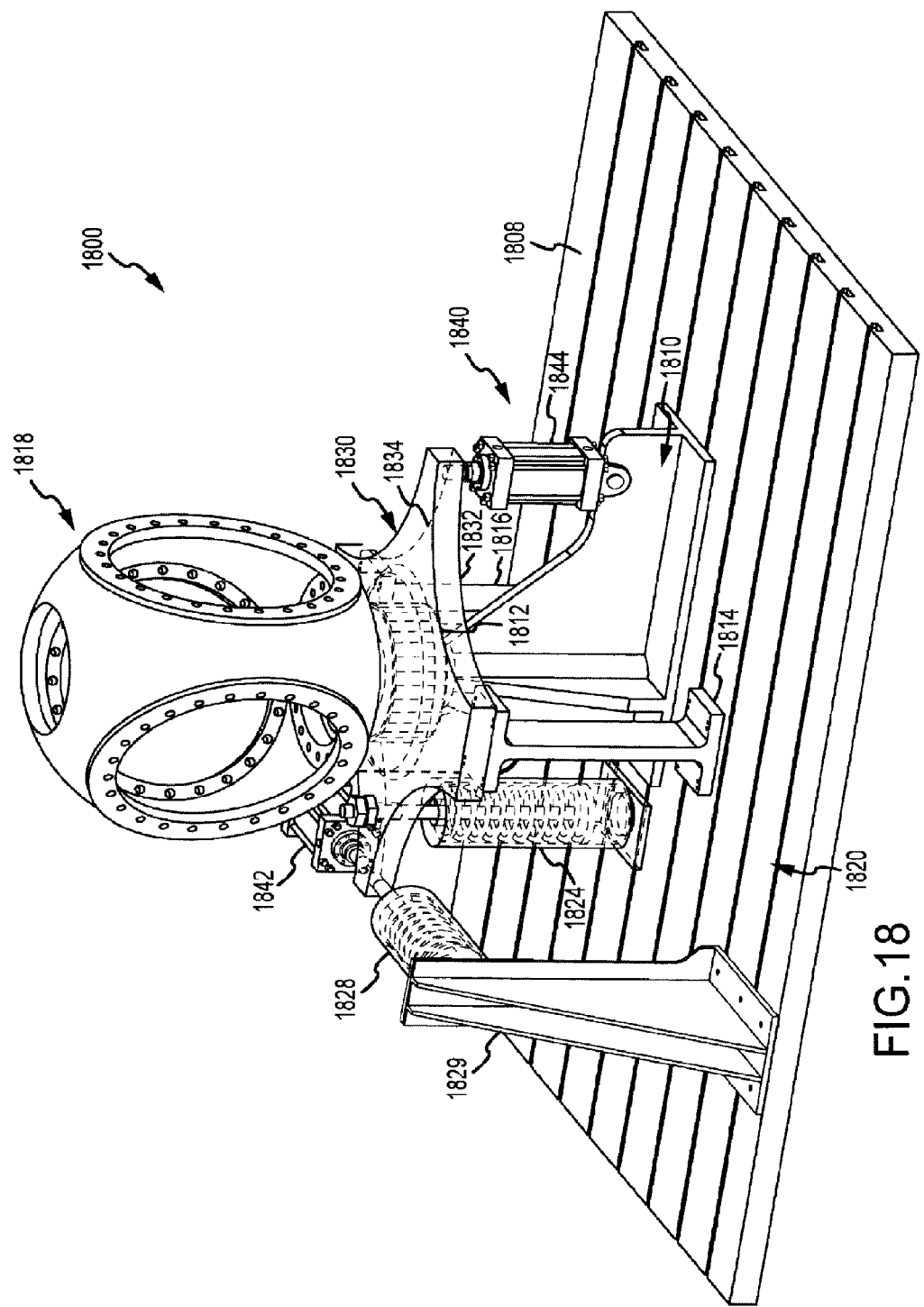
FIGS. 18 and 19 illustrate another vertical orientation BETS.
Figure 19:
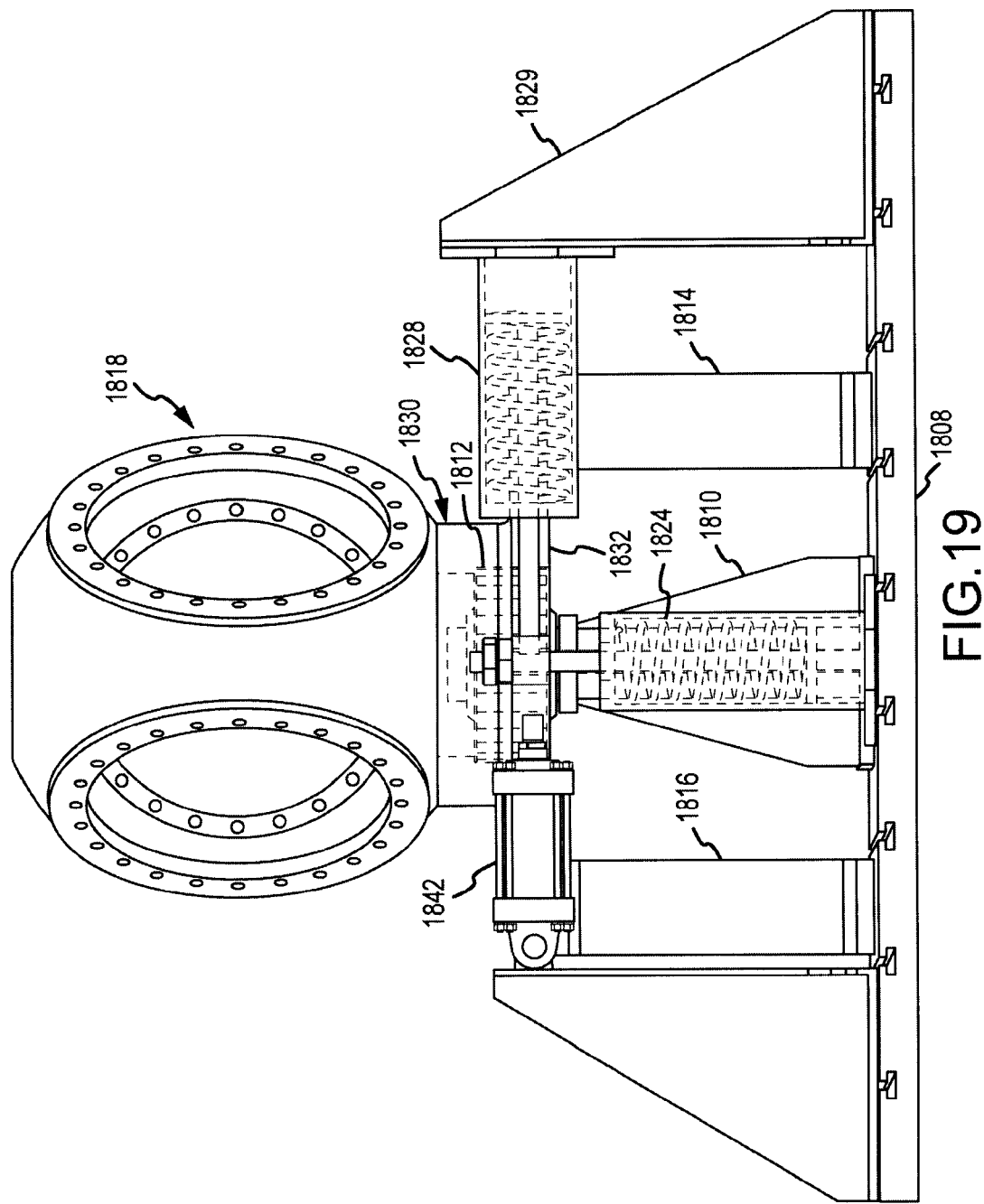

FIGS. 18 and 19 illustrate a BETS 1800 differing from BETS 1700 but arranged with a vertical orientation of the restoring spring assembly 1820, and, particularly, with the secondary tuning spring element 1824 arranged or positioned with its longitudinal axis extending vertically or substantially so (e.g., traverse to a test platform 1808). The BETS 1800 generally provides a functionality similar to the BETS 1700 but with a differing arrangement of its components, but there are a number of differences between this configuration and the horizontal configuration of the BETS shown in FIGS. 11-16. For example, a wind turbine hub 1818 is included in the test performed by the BETS 1800. Further, the BETS 1800 is vertically orientated, and the BETS base or blade mounting plate 1830 is excited in torsion in order to excite the blade in an edgewise direction. In embodiment 1800 of the BETS, restraint or restraints 1814, 1816 are added to stiffen the pitch degree of freedom and provide vertical support columns that also provide flap stiffness (but, of course, with an actuator one could also excite the pitch degree of freedom to make it a tri-axial BETS). An optional bearing guide 1812 is shown for redundancy during operation and to help ensure the DOF of interest is being excited during operation of the BETS 1800.

In the illustrated embodiment, the system 1800 includes a support assembly 1814, 1816, a restoring spring assembly 1824, and an excitation input assembly 1840. The support assembly 1810 may take the form of a vertical support as shown that is mounted to the test platform or foundation 1808 and at an opposite end supports the optional spherical bearing guide 1812, which may be interconnect with a blade mounting plate 1830. The restoring spring assembly 1820 is vertically arranged and includes a primary or flapwise spring element 1824 that extends vertically (or substantially so) from the platform 1808 to an inner or first side of a blade mounting plate 1830. In this example, the primary or flapwise spring element 1824 is attached to an arm or extension of the blade mounting plate 1830. The restoring spring assembly 1820 further may include an edge spring element 1828 that also contacts the arm or extension of the blade mounting plate 1830 (an edge of the plate 1830), and the edge spring element is supported at the other end by a vertical restraint 1829. Tuning spring members are not shown in this example but may be provided to tune the BETS 1800 in the flapwise direction, the edgewise direction, the pitch direction, and/or a combination thereof.

The system or BETS 1800 includes an excitation input assembly 1840 which may include mechanisms for imparting excitation forces or displacements to the blade mounting plate 1830, which is then at least in part restored or returned by the restoring spring assembly 1820 with spring elements 1824, 1828. As shown, an actuator 1844 is provided to excite the blade mounting plate 1830 to excite hub 1818 (which provides a blade mounting face), which may be used to retain a blade base (not shown in FIGS. 18 and 19 but providing a mounting with stiffness and other characteristics as found in use in the field). The flapwise actuator 1844 extends vertically and is mounted at one end to the support 1810 and in abutting contact at the other end with the inner or first surface 1832 of the blade mounting plate 1830 (or an arm/extension of the plate 1830, which may be opposite of the arm to which the primary or flapwise spring element 1824 is attached to). The excitation input assembly 1840 also includes an edgewise actuator 1842 that is supported at one end with a vertical restraint similar to restraint 1829 and in abutting contact at the other end to the blade mounting plate 1830 (e.g., to an extension or arm of the plate 1830 such as the same one as contacted by restoring spring elements 1824, 1828). Only one actuator is shown for each of the flapwise and edgewise directions, but other embodiments of BETS 1800 may include two or more actuators in one or both of these excitation directions. Similarly, restraints 1814, 1816 are shown to stiffen the pitch degree of freedom, but an actuator(s) may be added as shown in FIG. 17 or the like to excite the plate 1830 and hub 1818 (and base of an attached blade) in the pitch degree of freedom so as to make the BETS 1800 a tri-axial blade testing system.

The primary springs or spring elements may take a variety of forms such as solid shaft that are metallic (e.g., steel or the like) or non-metallic (e.g., fiberglass or the like). Also, the secondary or tuning spring elements may take a variety of forms to implement the testing systems described such as coil springs, torsion bars, hydraulic accumulators, and the like or a combination thereof.

The invention claimed is:

1. An apparatus for fatigue testing elongate test articles including wind turbine blades, comprising:
a test stand;
a restoring spring assembly mounted on the test stand, wherein the restoring spring assembly includes a primary spring element extending outward from the test stand and a blade mounting plate attached to an end of the primary spring element distal to the test stand, the blade mounting plate adapted for receiving and supporting a base of an elongate test article, whereby the supported base is pivotally mounted to the test stand via the restoring spring assembly; and
an excitation input assembly interconnected with the blade mounting plate to selectively apply excitation forces in a first direction and a second direction differing from the first direction.

2. The apparatus of claim 1, further comprising at least one tuning spring member positioned adjacent the primary spring element and extending between the test stand and the blade mounting plate.

3. The apparatus of claim 2, wherein the test article comprises a wind turbine blade, wherein the first and second directions are flapwise and edgewise directions of the wind turbine blade, and wherein at least one said at least one tuning spring member is positioned within the restoring spring assembly to increase a stiffness of the restoring spring assembly in the flapwise direction or the flapwise direction.

4. The apparatus of claim 3, wherein the at least one said at least one tuning spring member comprises a solid rod having an outer diameter less than an outer diameter of the primary spring element.

5. The apparatus of claim 1, wherein the blade mounting plate comprises an inner side proximate to the test stand that extends transverse to a longitudinal axis of the primary spring element and wherein the excitation input assembly comprises an actuator mounted to the test stand and coupled to the inner side to provide the excitation forces in the first or the second direction.

6. The apparatus of claim 5, wherein the excitation input assembly comprises an additional actuator coupled to the blade mounting plate to apply a portion of the excitation forces in a substantially vertical direction.

7. The apparatus of claim 1, wherein the primary spring element comprises an elongate solid metallic shaft with a circular cross section having an outer diameter greater than about 10 inches and a length of at least about 18 inches and wherein a central longitudinal axis of the primary spring element substantially coincides with a longitudinal axis of one of the elongate test articles mounted on the blade mounting plate.

8. A base excitation test system for fatigue testing wind turbine blades, comprising:
a test platform;
a spring restoring assembly with a base attached to the test platform, the spring restoring assembly comprising a blade mounting plate spaced apart from and above the base and receiving a blade hub adapted for rigidly supporting a base of a wind turbine blade and wherein the spring restoring assembly further comprises a primary spring element vertically extending between the base and the blade mounting plate;
a first actuator operable to apply first excitation forces on the blade mounting plate in a first direction; and a second actuator operable to apply second excitation forces on the blade mounting plate in a second direction generally orthogonal to the first direction, wherein the hub oscillates in more than one direction based on the applied first and second excitation forces and wherein the primary spring element applies restoring forces to the blade mounting plate to return the hub to an original, at rest position.

9. The system of claim 8, wherein the first excitation forces excite the wind turbine blade in an edge direction and wherein the spring restoring assembly further comprises an edge spring element extending parallel to the first actuator modifying a stiffness of the spring restoring assembly in the edge direction.

10. The system of claim 8, wherein the second excitation forces excite the wind turbine blade in a flap direction and wherein the spring restoring assembly further comprises a flap spring element extending parallel to the second actuator modifying a stiffness of the spring restoring assembly in the edge direction.

11. The system of claim 10, wherein the second actuator is coupled to the base and to the blade mounting plate and is spaced apart from the primary spring element and wherein the spring restoring assembly comprises an additional flap spring element extending parallel to the second actuator with the primary spring element disposed between the flap spring element and the additional flap spring element.

12. The system of claim 10, further comprising a third actuator operable to apply third excitation forces on the blade mounting plate in a third direction parallel to the second direction, wherein the third excitation forces excite the wind turbine blade in a pitch direction.

13. The system of claim 12, wherein the third actuator is coupled to the base and to the blade mounting plate and wherein the spring restoring assembly further comprises a pitch spring extending between the base and the blade mounting plate increasing a stiffness of the spring restoring assembly in the pitch direction.

14. The system of claim 13, wherein the pitch spring extends parallel to the flap spring and is positioned proximal to the third actuator.

15. An apparatus for fatigue testing a wind turbine blade, comprising:
a blade support including a restoring spring assembly with a blade mounting plate adapted for supporting a base of a wind turbine blade, wherein the restoring spring assembly includes a primary spring element attached to an opposite side of the blade mounting plate, whereby the supported base is pivotally supported by the blade support; and
an excitation input assembly interconnected with the blade mounting plate to selectively apply first and second excitation forces to concurrently excite the supported base in a flapwise direction and in an edgewise direction.

16. The apparatus of claim 15, wherein the restoring spring assembly further comprises a tuning spring adjusting the spring constant of the restoring spring assembly in the edgewise direction or in the flapwise direction.

17. The apparatus of claim 15, wherein the blade mounting plate comprises an inner side proximate to a test stand and wherein the excitation input assembly comprises first and second actuators mounted to the test stand and coupled to the inner side to provide the first and second excitation forces, respectively.

18. The apparatus of claim 15, wherein the primary spring element comprises an elongate solid shaft with a circular cross section having an outer diameter greater than about 10 inches and a length of at least about 18 inches.

19. The apparatus of claim 18, wherein a central longitudinal axis of the primary spring element substantially coincides with a longitudinal axis of the wind turbine blade mounted on the blade mounting plate.

20. The apparatus of claim 18, wherein the restoring spring assembly further comprises a plurality of tuning springs extending parallel to the primary spring element and the tuning springs each having a spring constant less than the primary spring element.

* * * * *